United States Patent
Galanis et al.

(10) Patent No.: US 11,865,150 B2
(45) Date of Patent: Jan. 9, 2024

(54) MATERIALS AND METHODS FOR TREATING CANCER

(71) Applicant: Mayo Foundation for Medical Education and Research, Rochester, MN (US)

(72) Inventors: Evanthia Galanis, Rochester, MN (US); S. Keith Anderson, Rochester, MN (US); Cheyne B. Kurokawa, Rochester, MN (US); Ianko D. Iankov, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 1120 days.

(21) Appl. No.: 16/477,830

(22) PCT Filed: Jan. 11, 2018

(86) PCT No.: PCT/US2018/013324
§ 371 (c)(1),
(2) Date: Jul. 12, 2019

(87) PCT Pub. No.: WO2018/132571
PCT Pub. Date: Jul. 19, 2018

(65) Prior Publication Data
US 2019/0365836 A1    Dec. 5, 2019

Related U.S. Application Data

(60) Provisional application No. 62/532,709, filed on Jul. 14, 2017, provisional application No. 62/446,131, filed on Jan. 13, 2017.

(51) Int. Cl.
*A61K 39/12* (2006.01)
*A61K 35/768* (2015.01)
(Continued)

(52) U.S. Cl.
CPC .......... *A61K 35/768* (2013.01); *A61K 31/519* (2013.01); *C12N 15/86* (2013.01);
(Continued)

(58) Field of Classification Search
None
See application file for complete search history.

(56) References Cited

U.S. PATENT DOCUMENTS

2013/0059749 A1   3/2013  Filipowicz et al.
2017/0039343 A1*  2/2017  Smith .................... G16B 20/00

FOREIGN PATENT DOCUMENTS

WO   WO-2011134670 A2 *  11/2011  ....... G01N 33/57484
WO   WO 2013/112942       8/2013
(Continued)

OTHER PUBLICATIONS

Turnbull et al., "Evidence for Oncolytic Virotherapy: Where Have We Got to and Where Are We Going?", Viruses 7:6291-6312 (Year: 2015).*

(Continued)

*Primary Examiner* — M Franco G Salvoza
(74) *Attorney, Agent, or Firm* — Fish & Richardson P.C.

(57) ABSTRACT

This document provides methods and materials involved in treating cancer. For example, methods and materials for using an inhibitor of UFM1 activity or expression and/or an inhibitor of UFL1 activity or expression to reduce a cancer cell's ability to carry out a DDR, thereby increasing the sensitivity of cancer cells to treatment with a DNA damaging therapy such as radiation or chemotherapy, are provided.

10 Claims, 19 Drawing Sheets

Specification includes a Sequence Listing.

(51) Int. Cl.
    A61K 31/519    (2006.01)
    C12N 15/86     (2006.01)
    G01N 33/574    (2006.01)
(52) U.S. Cl.
    CPC ............ G01N 33/57484 (2013.01); C12N 2760/18432 (2013.01)

(56) References Cited

FOREIGN PATENT DOCUMENTS

| WO | WO 2016/038119 | | 3/2016 | |
|---|---|---|---|---|
| WO | WO-2016057705 | A1 * | 4/2016 | ......... A61K 39/0011 |
| WO | WO-2016119052 | A1 * | 8/2016 | ......... A61K 31/4015 |
| WO | WO-2016149366 | A1 * | 9/2016 | |

OTHER PUBLICATIONS

Kurokawa et al., "Effects of the Innate Immune System on Oncolytic Measles Virotherapy," Mol. Therapy, May 2015, 23(S1):S32.

Liikanen et al., "Induction of Interferon Pathways Mediates In Vivo Resistance to Oncolytic Adenovirus," Mol. Therapy, Oct. 2011, 19(10):1858-1866.

Vähä-Koskela et al., "Tumor Restrictions to Oncolytic Virus," Biomedicines, Apr. 17, 2014, 2(2):163-194.

Worschech et al., "Systemic treatment of xenografts with vaccinia virus GLV-1h68 reveals the immunologic facet of oncolytic therapy," BMC Genomics, July 7, 2009, 10(1):301, 22 pages.

Andtbacka et al., "Talimogene Laherparepvec Improves Durable Response Rate in Patients With Advanced Melanoma," J. Clin. Oncol., 33(25):2780-8, Sep. 2015.

Bell and McFadden, "Viruses for Tumor Therapy," Cell Host Microbe, 15(3):260-5, Mar. 2014.

Brandes et al., "MGMT promoter methylation status can predict the incidence and outcome of pseudoprogression after concomitant radiochemotherapy in newly diagnosed glioblastoma patients," J. Clin. Oncol., 26(13):2192-7, May 2008.

Chawla-Sarkar et al., Preferential induction of apoptosis by interferon (IFN)—beta compared with IFN-alpha2: correlation with TRAIL/Apo2L induction in melanoma cell lines. Clin. Cancer Res., 7(6):1821-31, Jun. 2001.

Critchley-Thorne et al., "Impaired interferon signaling is a common immune defect in human cancer," Proc. Natl. Acad. Sci. USA 106:9010-5, Jun. 2009.

Del Rio et al., "Gene expression signature in advanced colorectal cancer patients select drugs and response for the use of leucovorin, fluorouracil, and irinotecan," J. Clin. Oncol., 25(7):773-80, Mar. 2007.

Dennis et al., "Multiplexed Cancer Immune Response Analysis nCounter® PanCancer Immune Profiling Panel for Gene Expression," NanoString Tech., 1:20140909, Sep. 2014.

Devaux et al., "Measles Virus Phosphoprotein Gene Products: Conformational Flexibility of the P/V Protein Amino-Terminal Domain and C Protein Infectivity Factor Function," J. Virol., 78(21):11632-40, Nov. 2004.

Devaux et al., "The measles virus phosphoprotein interacts with the linker domain of STAT1," Virology 444(1-2):250-6, Sep. 2013.

Dingli et al., "Image-guided radiovirotherapy for multiple myeloma using a recombinant measles virus expressing the thyroidal sodium iodide symporter," Blood, 103(5):1641-6, Mar. 2004.

Dudoit et al., "Comparison of Discrimination Methods for the Classification of Tumors Using Gene Expression Data," J. Am. Stat, Assoc., 97(457):77-87, 2002.

Duprex et al., "Observation of Measles Virus Cell-to-Cell Spread in Astrocytoma Cells by Using a Green Fluorescent Protein-Expressing Recombinant Virus," J. Virol., 73(11):9568-75, Nov. 1999.

Engeland et al., "CTLA-4 and PD-L1 checkpoint blockade enhances oncolytic measles virus therapy," Mol. Ther., 22(11):1949-59, Nov. 2014.

Galanis et al., "Phase I trial of intraperitoneal administration of an oncolytic measles virus strain engineered to express carcinoembryonic antigen for recurrent ovarian cancer," Cancer Res., 70(3):875-82, Jan. 2010.

Giannini et al., "Patient tumor EGFR and PDGFRA gene amplifications retained in an invasive intracranial xenograft model of glioblastoma multiforme," NeuroOncol, 7(2):164-76, Apr. 2005.

Goujon et al., "Human MX2 is an interferon-induced post-entry inhibitor of HIV-1 infection," Nature, 502(7472):559-62, Sep. 2013.

Guerra et al., "Vaccinia virus E3 protein prevents the antiviral action of ISG15," PLoS Pathog., 4:e1000096, Jul. 2008.

Haralambieva et al., "Engineering oncolytic measles virus to circumvent the intracellular innate immune response," Mol. Ther., 15(3):588-97, Mar. 2007.

He et al., "Significant antitumor activity of oncolytic adenovirus expressing human interferon-beta for hepatocellular carcinoma," J. Gene Med. 10(9):983-92, Aug. 2008.

Iankov et al., "Converting Tumor-specific Markers Into Reporters of Oncolytic Virus Infection," Mol. Ther, 17(8):1395-403, Aug. 2009.

Iankov et al., "Expression of immunomodulatory neutrophil-activating protein of Helicobacter pylori enhances the antitumor activity of oncolytic measles virus," Mol. Ther., 20(6):1139-47, Jun. 2012.

Jenks et al., "Safety studies on intrahepatic or intratumoral injection of oncolytic vesicular stomatitis virus expressing interferon-beta in rodents and nonhuman primates," Hum. Gene Ther., 21(4):451-62, Mar. 2010.

Johns et al, "Antiproliferative potencies of interferons on melanoma cell lines and xenografts: higher efficacy of interferon beta," J. Natl. Cancer Inst., 84(15):1185-90, Aug. 1992.

Kalari et al., "MAP-RSeq: Mayo Analysis Pipeline for RNA sequencing," BMC Bioinformatics, 15:224, Jun. 2014.

Kato et al., "Length-dependent recognition of double-stranded ribonucleic acids by retinoic acid-inducible gene-I and melanoma differentiation-associated gene," J. Exp. Med., 205(7):1601-10, Jun. 2008.

Kim et al., "TopHat2: accurate alignment of transcriptomes in the presence of insertions, deletions and gene fusions," Genome Biol., 14(4):R36, Apr. 2013.

Kurokawa et al., "Abstract #642:Pre-existing antiviral state can impact infection in glioblastoma patients treated with oncolytic Measles Virus," Poster, Presented at American Society of Gene and Cell Therapy meeting, 2014, 1 page.

Kurokawa et al., "Impact of the Innate Immune System on Oncolytic Measles Virotherapy," PowerPoint, Presented at American Society of Gene and Cell Therapy meeting, 2015, 1 page.

Kurokawa et al.., "73. Effects of the Innate Immune System on Oncolytic Measles Virotherapy.," Mol. Ther., 23(Supp. 1):S32, May 2015.

Langfield et al., "Manufacture of Measles Viruses," Viral Vectors Gene Ther., 737:345-66, Apr. 2011.

Langmead et al., "Ultrafast and memory-efficient alignment of short DNA sequences to the human genome," Genome Biol., 10(3):R25, Mar. 2009.

Msaouel et al., "Oncolytic measles virus strains as novel anticancer agents," Expert Opin. Biol. Ther., 13(4):483-502, Jan. 2013.

Nakatsu et al., "Measles Virus Circumvents the Host Interferon Response by Different Actions of the C and V Proteins," J. Virol., 82(17):8296-306, Aug. 2008.

Noser et al., "The RAS/Raf1/MFK/ERK signaling pathway facilitates VSV-mediated oncolysis: implication for the defective interferon response in cancer cells," Mol. Ther., 15(8):1531-6, Aug. 2007.

Paik et al., "A multigene assay to predict recurrence of tamoxifen-treated, node-negative breast cancer," N. Engl. J. Med., 351(127):2817-26, Dec. 2004.

Paraskevakou et al., "Epidermal Growth Factor Receptor (EGFR)—Retargeted Measles Virus Strains Effectively Target EGFR- or EGFRvIII Expressing Gliomas," Mol. Ther., 15(4):677-86, Apr. 2007.

PCT International Perliminary Report on Patentability in International Appln. No. PCT/US2018/013324 dated Jul. 25, 2019, 10 pages.

(56) References Cited

OTHER PUBLICATIONS

PCT International Search Report and Written Opinion in International Appln. No. PCT/US2018/013324 dated May 15, 2018, 15 pages.
Peng et al. "Intraperitoneal Therapy of Ovarian Cancer Using an Engineered Measles Virus," Cancer Res., 62(16):4656-62, Aug. 2002.
Phipps-Yonas et al., "Interferon-β Pretreatment of Conventional and Plasmacytoid Human Dendritic Cells Enhances Their Activation by Influenza Virus," PLoS Pathog., 4(10):e1000193, Oct. 2008.
Pichlmair et al., "RIG-I-mediated antiviral responses to single-stranded RNA bearing 5'-phosphates," Science, 314(5801):997-1001, Nov. 2006.
Russell et al., "Remission of disseminated cancer after systemic oncolytic virotherapy," Mayo Clin. Proc., 89(7):926-33, Jul. 2014.
Salonga et al., "Colorectal tumors responding to 5-fluorouracil have low gene expression levels of dihydropyrimidine dehydrogenase, thymidylate synthase, and thymidine phosphorylase," Clin. Cancer Res., 6:(4)1322-7, Apr. 2000.
Schoggins, "Interferon-stimulated genes: roles in viral pathogenesis," Curr. Opin. Virol., 6:40-6, Jun. 2014.
Seth et al., "Antiviral innate immunity pathways," Cell Res., 16(2):141-7, Feb. 2006.
Shi et al., "Positive regulation of interferon regulatory factor 3 activation by Herc5 via ISG15 modification," Mol. Cell Biol., 30(10):2424-36, Mar. 2010.
Shingai et al., "Differential type I IFN-inducing abilities of wild-type versus vaccine strains of measles virus," J. Immunol., 179(9):6123-33, Nov. 2007.
Silvennoinen et al., "Interferon-induced nuclear signalling by Jak protein tyrosine kinases," Nature, 366(6455):583-5, Dec. 1993.
Staeheli and Pavlovic, "Inhibition of vesicular stomatitis virus mRNA synthesis by human MxA protein," J. Virol., 65(8):4498-501, Aug. 1991.
Stewart et al., "Inhibitors of the interferon response enhance virus replication in vitro," PLoS One, 9(11):e112014, Nov. 2014.
Stojdl et al., "Exploiting tumor-specific defects in the interferon pathway with a previously unknown oncolytic virus," Nat. Med., 6(7):821-5, Jul. 2000.
Trapnell et al., "How to map billions of short reads onto genomes," Nat. Biotechnol., 27(5):455-7, May 2009.
Venet et al., "Most random gene expression signatures are significantly associated with breast cancer outcome," PLoS Comput. Biol., 7(10):e1002240, Oct. 2011.
Zamarin et al., "Localized oncolytic virotherapy overcomes systemic tumor resistance to immune checkpoint blockade immunotherapy," Sci. Transl. Med., 6(226):226ra32, Mar. 2014.
Devaux et al., "Tyrosine 110 in the measles virus phosphoprotein is required to block STAT1 phosphorylation," Virology, Mar. 30, 2007, 360(1):72-83.
Iankov et al., "30. Gene Expression Profile of Innate Immune Anti-Viral Factors in Ovarian Cancer Patients Treated with Oncolytic Measles Virus," Mol. Therapy, May 2014, 22(S1):S12.
Iankov et al., "417. Gene Expression Profiling Identifies Predictive Markers of Response to Oncolytic Measles Virus Therapy," Mol Therapy, May 2013, 21(S1):S160.
Iankov et al., "Gene expression profiling identifies predictive markers of response to oncolytic measles virus therapy," Poster, Presented at Proceedings of the American Society of Gene & Cell Therapy 16th Annual Meeting, Salt Lake City, UT, USA, May 15-18, 2013, 1 page.
Kurokawa et al., "642. Pre-Existing Antiviral State Can Impact Oncolytic Infection in Glioblastoma Patients Treated With Oncolytic Measles Virus," Mol. Therapy, May 2014, 22(S1):S248.
Ohno et al., "Dissection of measles virus V protein in relation to its ability to block alpha/beta interferon signal transduction," Virology, Oct. 2004, 85(Pt 10):2991-2999.
Seo et al., "Viperin: a multifunctional, interferon-inducible protein that regulates virus replication," Cell Host Microbe, Dec. 15, 2011, 10(6):534-539.
ClinicalTrials.gov [online], "Viral Therapy in Treating Patients With Recurrent Glioblastoma Multiforme," NCT00390299, last updated Jan. 2, 2020, retrieved on Jun. 26, 2023, retrieved from URL<https://classic.clinicaltrials.gov/ct2/show/NCT00390299>, 39 pages.
Ruotsalainen et al., "Clonal variation in interferon response determines the outcome of oncolytic virotherapy in mouse CT26 colon carcinoma model," Gene Ther., Jan. 2015, 22(1):65-75.

* cited by examiner

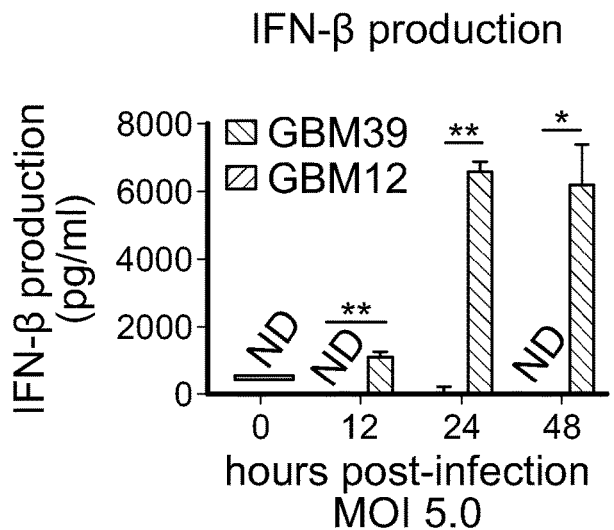
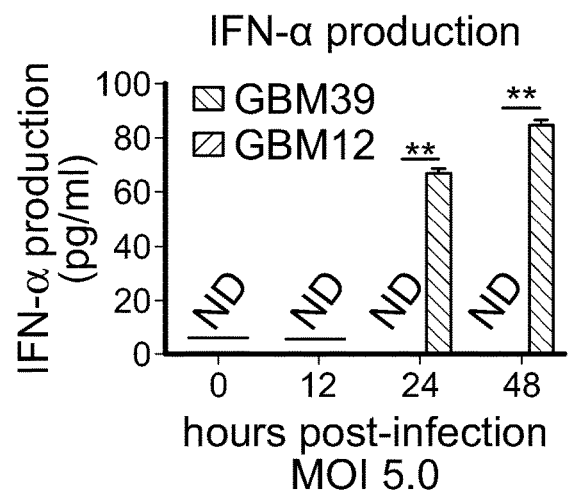
FIG. 1G
FIG. 1H
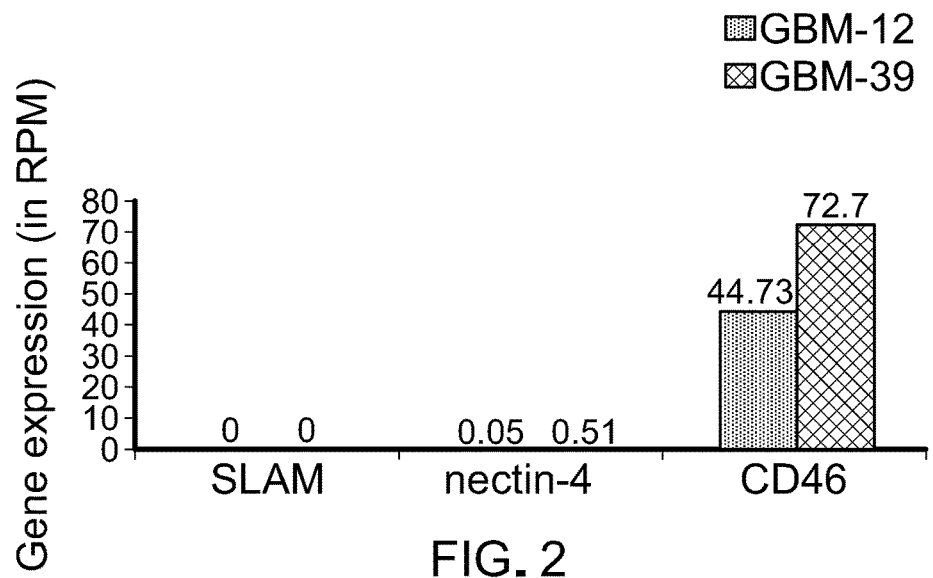
FIG. 2

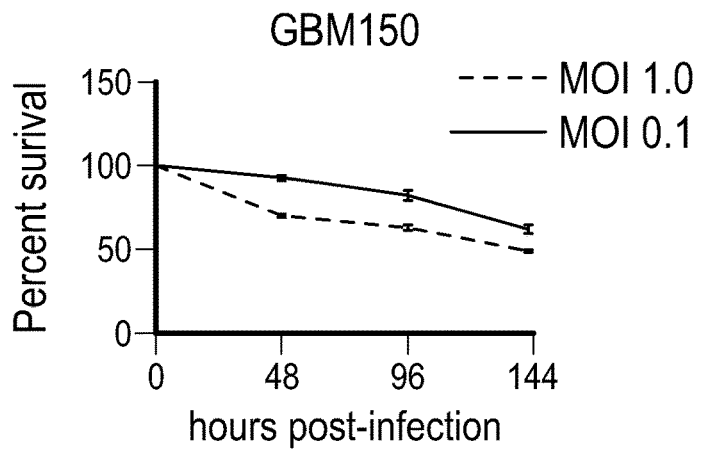

FIG. 3E

| Pathway | P-value |
| --- | --- |
| Protein binding | 6.12E-31 |
| Type I interferon-mediated signaling pathway | 2.14E-20 |
| Nucleotide binding | 9.08E-18 |
| Cytokine-mediated signaling pathway | 2.33E-17 |
| Metal ion binding | 3.43E-17 |
| ATP binding | 2.3E-14 |
| Immune response | 8.38E-14 |
| Signal transduction | 1.12E-13 |
| Interferon-gamma mediated signaling pathway | 6.18E-13 |
| Sequence-specific DNA binding transcription factor activity | 1.49E-11 |
| Calcium ion binding | 1.61E-10 |
| Multicellular organismal development | 9.57E-10 |
| Zinc ion binding | 2.89E-09 |
| Protein processing in endoplasmic reticulum | 4.09E-09 |
| Hydrolase activity | 7.11 E-09 |

FIG. 3F

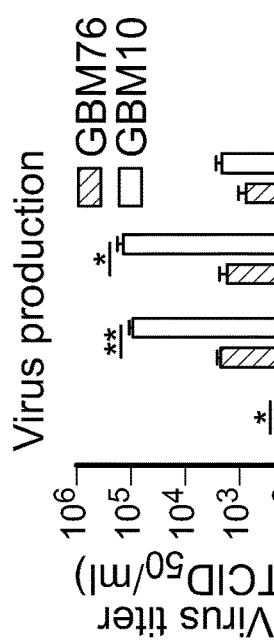
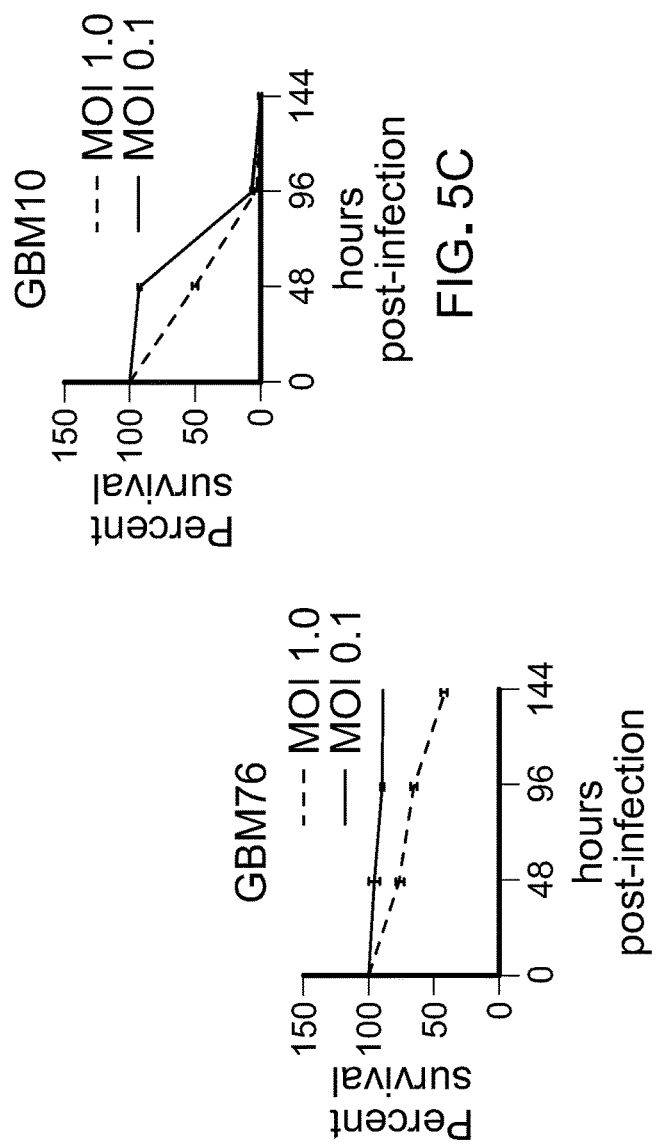
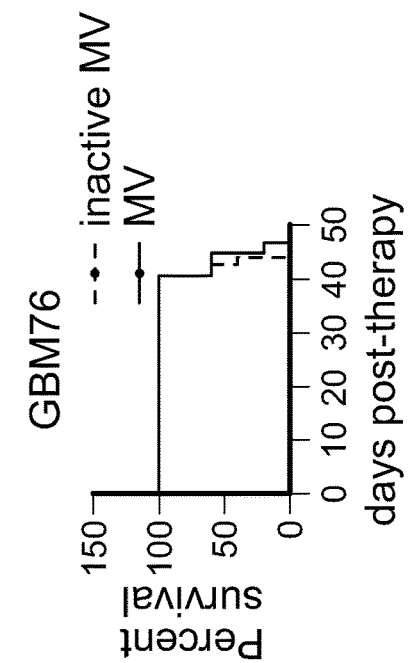
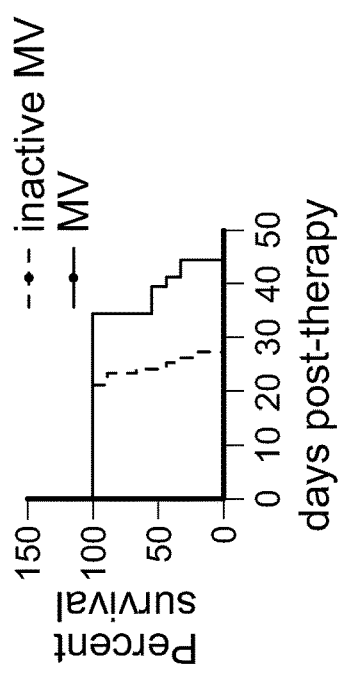
FIG. 5B  FIG. 5C  FIG. 5D  FIG. 5E  FIG. 5F

| Patient | Dose TCID$_{50}$ | Genome copies/ug RNA | Tumor section with detectable virus |
|---|---|---|---|
| Pt 1 | $2 \times 10^6$ | $6 \times 10^7$ | 2/3 |
| Pt 2 | $2 \times 10^6$ | Not Available | Not Available |
| Pt 3 | $2 \times 10^6$ | $3.8 \times 10^4$ | 3/5 |
| Pt4 | $2 \times 10^7$ | $4.1 \times 10^4$ | 3/5 |
| Pt5 | $2 \times 10^7$ | $1.3 \times 10^5$ | 10/23 |
| Pt6 | $2 \times 10^7$ | $1.7 \times 10^5$ | 3/3 |
| Pt7 | $2 \times 10^7$ | $1.3 \times 10^3$ | 2/3 |
| Pt8 | $2 \times 10^7$ | $6.8 \times 10^6$ | 4/4 |
| Pt9 | $2 \times 10^7$ | $1.2 \times 10^4$ | 4/4 |
| P10 | $2 \times 10^7$ | 0 | 0/4 | hours post MV infection

Virus production 72 h post-infection
MOI 0.1

| Patient | Virus | Dose | DLDA Score | Prediction | PFS |
|---|---|---|---|---|---|
| *OV-1551 | MV-CEA | $10^6$ | -333.0 | Responder | NE |
| OV-1029 | MV-CEA | $10^3$ | -241.7 | Responder | 9.0 |
| OV-1002 | MV-CEA | $10^3$ | -161.0 | Responder | 3.6 |
| OV-1485 | MV-CEA | $10^4$ | 283.8 | Non-responder | 0.8 |
| OV-1355 | MV-CEA | $10^6$ | 922.0 | Non-responder | 1.7 |
| OV-1553 | MV-CEA | $10^5$ | 1019.1 | Non-responder | 1.8 |
| OV-1127 | MV-CEA | $10^6$ | 1361.4 | Non-responder | 0.8 |

*Pt 1551 was removed from study because of treatment unrelated infection (peritonitis) following one treatment cycle
NE = not evaluable

```
                        SEQUENCE LISTING

<160> NUMBER OF SEQ ID NOS: 3

<210> SEQ ID NO 1
<211> LENGTH: 16
<212> TYPE: DNA
<213> ORGANISM: Artificial Sequence
<220> FEATURE:
<223> OTHER INFORMATION: synthetic primer

<400> SEQUENCE: 1
gggtgtgccg gttgga                                               16

<210> SEQ ID NO 2
<211> LENGTH: 22
<212> TYPE: DNA
<213> ORGANISM: Artificial Sequence
<220> FEATURE:
<223> OTHER INFORMATION: synthetic primer

<400> SEQUENCE: 2
agaagccagg gagagctaca ga                                        22

<210> SEQ ID NO 3
<211> LENGTH: 23
<212> TYPE: DNA
<213> ORGANISM: Artificial Sequence
<220> FEATURE:
<223> OTHER INFORMATION: synthetic probe

<400> SEQUENCE: 3
tgggcagctc tcgcatcact tgc                                       23
```

MATERIALS AND METHODS FOR TREATING CANCER

CROSS-REFERENCE TO RELATED APPLICATIONS

This application is a National Stage application under 35 U.S.C. § 371 of International Application No. PCT/US2018/013324, having an International Filing Date of Jan. 11, 2018, which claims priority to U.S. Application Ser. No. 62/532,709, filed on Jul. 14, 2017 and U.S. Application Ser. No. 62/446,131, filed on Jan. 13, 2017. The disclosure of the prior applications are considered part of the disclosure of this application, and are incorporated in its entirety into this application.

FEDERAL FUNDING STATEMENT

This invention was made with government support under CA200507 awarded by the National Institutes of Health. The government has certain rights in the invention.

BACKGROUND

1. Technical Field

This document relates to materials and methods involved in treating cancer. For example, this document provides materials and methods for using one or more oncolytic viruses (e.g., one or more oncolytic viruses) to treat cancer in a mammal (e.g., a human) identified as having a cancer likely to respond to oncolytic virotherapy.

2. Background Information

Oncolytic viruses are cancer therapies that employ engineered or naturally evolved viruses of cancer tropism to incite tumor cell death in the treated patient. In general, when a replicating oncolytic virus is inoculated into a tumor, infected tumor cells have the potential to produce progeny virus, allowing destructive infection to spread to neighboring tumor cells. The potential for virus replication is determined by the cell's ability to sense and respond to the viral infection. However, clinical oncolytic virotherapy trials for the treatment of several tumor types have seen limited success (Russell et al., *Mayo Clin. Proc.*, 89:926-933 (2014); Andtbacka et al., *J. Clin. Oncol.*, 25:2780-2788 (2015); and Bell et al., *Cell HostMicrobe*, 15, 260-265 (2014)).

SUMMARY

This document provides materials and methods for treating cancer. For example, this document provides materials and methods for determining the virotherapy responsiveness of cancer cells obtained from a mammal having cancer, and administering one or more optimal therapies for the mammal.

As demonstrated herein, an interferon (IFN)-stimulated gene (ISG) signature having increased expression of ISGs in the tumors of glioblastoma (GBM) and ovarian cancer (OvCa) patients treated with oncolytic MV correlated with minimal evidence of virus infection and resistance to virotherapy, while an ISG signature having decreased expression of ISGs correlated with responsiveness to virotherapy. The ISG signature in a cancer cell can be used in an analysis (e.g., a diagonal linear discriminant analysis (DLDA)) to predict virotherapy responsiveness. For example, an ISG signature can be used to obtain a virotherapy permissive score (e.g., a virotherapy permissive ISG signature) when an ISG signature that indicates that cancer cells (e.g., cells collected from a mammal having cancer) have significantly decreased expression levels of ISGs as compared to those expression levels observed in a control sample (e.g., a control GBM sample) with known responses to MV. In some cases, an ISG signature also can be used to obtain a virotherapy resistant score. Cancer cells obtained from a mammal having cancer can be assessed to determine virotherapy responsiveness of the cancer, and to select a treatment option for the mammal. For example, if cancer cells obtained from a mammal having cancer are identified as having a DLDA score less than 150, then the mammal can be classified as having a cancer responsive to treatment with one or more oncolytic viruses effective to kill cancer cells via viral replication or expression of virus-encoding therapeutic transgenes, including immunomodulatory and drug converting transgenes. A mammal having a cancer with a low DLDA score (e.g., less than −250) can be treated with, for example, administrations (e.g., intratumoral injections) of oncolytic viruses as the sole anti-cancer treatment agent. A mammal having a cancer with an intermediate DLDA score (e.g., about −250 to about 150) can be treated with, for example, one or more oncolytic viruses in combination with one or more immunomodulatory therapies (e.g., JAK/Stat inhibitors, immune checkpoint inhibitors, and/or modified virus vectors resistant to ISG effects). For example, if cancer cells obtained from a mammal having cancer are identified as having a high DLDA score (e.g., greater than 150), then the mammal can be classified as having a cancer that is resistant to treatment with an oncolytic virus. Such a mammal should not be treated with viruses as oncolytic agents, but can instead be treated with, for example, alternative cancer treatments (e.g., surgery and/or chemotherapy).

There is a need in the field of oncolytic virotherapy for a test that can determine whether or not a patient will be responsive to an administered oncolytic virus. The materials and methods described herein not only provide such a test, but the ability to pre-select the best candidates for virotherapy provides a major benefit in patient care and improved cost-effectiveness.

In general, one aspect of this document features a method for treating cancer in a mammal. The method includes, or consists essentially of, identifying a mammal as having cancer cells that have a virotherapy permissive interferon (IFN)-stimulated gene (ISG) signature, where the ISG signature includes at least 6 ISGs selected from the group consisting of HLA-A, HLA-B, HLA-C, HLA-E, HLA-G, IFI27, IFI35, IFI6, IFIT1, IFIT3, IRF1, IRF2, IRF9, ISGJ5, MX1, MX2, OAS1, OAS2, OAS3, OASL, SOCS1, and STAT2; and administering an oncolytic virus to the mammal under conditions where the number of cancer cells within the mammal is reduced. The mammal can be a human. The cancer can be glioblastoma. The cancer can be ovarian cancer. The oncolytic virus can be a measles virus. The virotherapy permissive ISG signature can include decreased levels of expression as compared to control cells. The control cells can include cancer cells resistant to oncolytic virus therapy. The ISG signature can include OAS2, OAS1, IFI6, HLA-C, IFIT1, and MX2. The ISG signature can include OAS2, OAS1, IFI6, HLA-C, IFIT1, MX2, HLA-A, IFIT3, OASL, HLA-G, MX1, and IRF1. The ISG signature can include HLA-A, HLA-B, HLA-C, HLA-E, HLA-G, IFI27, IFI35, IFI6, IFIT1, IFIT3, IRF1, IRF2, IRF9, ISG15, MX1, MX2, OAS1, OAS2, OAS3, OASL, SOCS1, and STAT2. The ISG signature can include at least one of HLA-G, OAS1, OAS3, or SOCS1. The ISG signature can include at least two of HLA-G, OAS1, OAS3, or SOCS1. The ISG signature can include at least three of HLA-G, OAS1, OAS3, or SOCS1. The ISG signature can include HLA-G, OAS1, OAS3, and SOCS1.

In another aspect, this document features a method for identifying a mammal as having cancer responsive to treatment with an oncolytic virus. The method includes, or consists essentially of, determining that cancer cells from a cancer have a virotherapy permissive ISG signature, where the ISG signature includes at least 6 ISGs selected from the group consisting of HLA-A, HLA-B, HLA-C, HLA-E, HLA-G, IFI27, IFI35, IFI6, IFIT1, IFIT3, IRF1, IRF2, IRF9, ISG15, MX1, MX2, OAS1, OAS2, OAS3, OASL, SOCS1, and STAT2; and classifying the mammal as having cancer responsive to treatment with the oncolytic virus. The mammal can be a human. The cancer can be glioblastoma. The method cancer can be ovarian cancer. The oncolytic virus can be a measles virus. The virotherapy permissive ISG signature can include decreased levels of expression as compared to control cells. The control cells can include cancer cells resistant to oncolytic virus therapy. The ISG signature can include OAS2, OAS1, IFI6, HLA-C, IFIT1, and MX2. The ISG signature can include OAS2, OAS1, IFI6, HLA-C, IFIT1, MX2, HLA-A, IFIT3, OASL, HLA-G, MX1, and IRF1. The ISG signature can include HLA-A, HLA-B, HLA-C, HLA-E, HLA-G, IFI27, IFI35, IFI6, IFIT1, IFIT3, IRF1, IRF2, IRF9, ISG15, MX1, MX2, OAS1, OAS2, OAS3, OASL, SOCS1, and STAT2. The ISG signature can include at least one of HLA-G, OAS1, OAS3, or SOCS1. The ISG signature can include at least two of HLA-G, OAS1, OAS3, or SOCS1. The ISG signature can include at least three of HLA-G, OAS1, OAS3, or SOCS1. The ISG signature can include HLA-G, OAS1, OAS3, and SOCS1.

In another aspect, this document features a method for treating cancer in a mammal. The method includes, or consists essentially of, identifying a mammal as having cancer cells that are responsive to treatment with one or more oncolytic viruses, and administering an oncolytic virus to the mammal under conditions where the number of cancer cells within the mammal is reduced. The mammal can be a human. The cancer can be glioblastoma. The cancer can be ovarian cancer. The oncolytic virus can be a measles virus. The cancer cells can exhibit a DLDA score of less than 150. Where the DLDA score is less than −250, the administering one or more oncolytic viruses can be the sole anti-cancer treatment agent. Where the DLDA score is about −250 to about 150, the method also can include administering one or more immunomodulatory agents to the mammal under conditions where the number of cancer cells within said mammal is reduced. The one or more immunomodulatory agents can be ruxolitinib, pembrolizumab, nivolumab, atezolizumab, durvalumab, and/or ipilimumab. The one or more immunomodulatory agents can include ruxolitinib. The identifying step can comprise determining the expression levels, within the cancer cells, of at least 6 genes selected from the group consisting of HLA-A, HLA-B, HLA-C, HLA-E, HLA-G, IFI27, IFI35, IFI6, IFIT1, IFIT3, IRF1, IRF2, IRF9, ISG15, MX1, MX2, OAS1, OAS2, OAS3, OASL, SOCS1, and STAT2. The at least 6 genes can include OAS2, OAS1, IFI6, HLA-C, IFIT1, and MX2. The at least 6 genes can include OAS2, OAS1, IFI6, HLA-C, IFIT1, MX2, HLA-A, IFIT3, OASL, HLA-G, MX1, and IRF1. The at least 6 genes can include HLA-A, HLA-B, HLA-C, HLA-E, HLA-G, IFI27, IFI35, IFI6, IFIT1, IFIT3, IRF1, IRF2, IRF9, ISG15, MX1, MX2, OAS1, OAS2, OAS3, OASL, SOCS1, and STAT2. The at least 6 genes can include at least one of HLA-G, OAS1, OAS3, or SOCS1. The at least 6 genes can include at least two of HLA-G, OAS1, OAS3, or SOCS1. The at least 6 genes can include at least three of HLA-G, OAS1, OAS3, or SOCS1. The at least 6 genes can include HLA-G, OAS1, OAS3, and SOCS1.

In another aspect, this document features a method for identifying a mammal as having cancer responsive to treatment with an oncolytic virus. The method includes, or consists essentially of, determining that cancer cells from said cancer have a DLDA score of less than 150, and classifying the mammal as having cancer responsive to treatment with the oncolytic virus. The mammal can be a human. The cancer can be glioblastoma. The cancer can be ovarian cancer. The oncolytic virus can be MV. When the DLDA score is about −250 to about 150. The method also can include classifying said mammal as having cancer responsive to treatment with one or more immunomodulatory agents.

The one or more immunomodulatory agents can be ruxolitinib, pembrolizumab, nivolumab, atezolizumab, durvalumab, and/or ipilimumab. The one or more immunomodulatory agents can include ruxolitinib. The determining step can comprise determining the expression levels, within the cancer cells, of at least 6 genes selected from the group consisting of HLA-A, HLA-B, HLA-C, HLA-E, HLA-G, IFI27, IFI35, IFI6, IFIT1, IFIT3, IRF1, IRF2, IRF9, ISG15, MX1, MX2, OAS1, OAS2, OAS3, OASL, SOCS1, and STAT2. The at least 6 genes can include OAS2, OAS1, IFI6, HLA-C, IFIT1, and MX2. The at least 6 genes can include OAS2, OAS1, IFI6, HLA-C, IFIT1, MX2, HLA-A, IFIT3, OASL, HLA-G, MX1, and IRF1. The at least 6 genes can include HLA-A, HLA-B, HLA-C, HLA-E, HLA-G, IFI27, IFI35, IFI6, IFIT1, IFIT3, IRF1, IRF2, IRF9, ISG15, MX1, MX2, OAS1, OAS2, OAS3, OASL, SOCS1, and STAT2. The at least 6 genes can include at least one of HLA-G, OAS1, OAS3, or SOCS1. The at least 6 genes can include at least two of HLA-G, OAS1, OAS3, or SOCS1. The at least 6 genes can include at least three of HLA-G, OAS1, OAS3, or SOCS1. The at least 6 genes can include HLA-G, OAS1, OAS3, and SOCS1.

In another aspect, this document features a method for identifying a mammal as having cancer resistant to treatment with an oncolytic virus. The method includes, or consists essentially of, determining that cancer cells from said cancer have a DLDA score of greater than 150, and classifying said mammal as having cancer resistant to treatment with said oncolytic virus. The mammal can be a human. The cancer can be glioblastoma. The cancer can be ovarian cancer. The oncolytic virus can be MV. The determining step can comprise determining the expression levels, within the cancer cells, of at least 6 genes selected from the group consisting of HLA-A, HLA-B, HLA-C, HLA-E, HLA-G, IFI27, IFI35, IFI6, IFIT1, IFIT3, IRF1, IRF2, IRF9, ISG15, MX1, MX2, OAS1, OAS2, OAS3, OASL, SOCS1, and STAT2. The at least 6 genes can include OAS2, OAS1, IFI6, HLA-C, IFIT1, and MX2. The at least 6 genes can include OAS2, OAS1, IFI6, HLA-C, IFIT1, MX2, HLA-A, IFIT3, OASL, HLA-G, MX1, and IRF1. The at least 6 genes can include HLA-A, HLA-B, HLA-C, HLA-E, HLA-G, IFI27, IFI35, IFI6, IFIT1, IFIT3, IRF1, IRF2, IRF9, ISG15, MX1, MX2, OAS1, OAS2, OAS3, OASL, SOCS1, and STAT2. The at least 6 genes can include at least one of HLA-G, OAS1, OAS3, or SOCS1. The at least 6 genes can include at least two of HLA-G, OAS1, OAS3, or SOCS1. The at least 6 genes can include at least three of HLA-G, OAS1, OAS3, or SOCS1. The at least 6 genes can include HLA-G, OAS1, OAS3, and SOCS1.

In another aspect, this document features a method for converting cancer resistant to treatment with an oncolytic virus into cancer responsive to treatment with an oncolytic virus. The method comprises, or consists essentially of, administering one or more immunomodulatory agents to a mammal identified as having the cancer resistant to treatment with an oncolytic virus. The mammal can be a human. The cancer can be glioblastoma. The cancer can be ovarian cancer. The oncolytic virus can be MV. The one or more immunomodulatory agents can be selected from the group consisting of ruxolitinib, pembrolizumab, nivolumab, atezolizumab, durvalumab, and ipilimumab. The one or more immunomodulatory agents can be ruxolitinib. Cancer cells of the cancer resistant to treatment with an oncolytic virus can be cancer cells that were identified as having a diagonal linear discriminant analysis (DLDA) score from about −250 to about 150. The mammal can be a mammal that was identified as having the cancer resistant to treatment with an oncolytic virus using a method comprising determining the expression levels, within cancer cells of the cancer, of at least 6 genes selected from the group consisting of HLA-A, HLA-B, HLA-C, HLA-E, HLA-G, IFI27, IFI35, IFI6, IFIT1, IFIT3, IRF1, IRF2, IRF9, ISG15, MX1, MX2, OAS1, OAS2, OAS3, OASL, SOCS1, and STAT2. The at least 6 genes can include OAS2, OAS1, IFI6, HLA-C, IFIT1, and MX2. The at least 6 genes can include OAS2, OAS1, IFI6, HLA-C, IFIT1, MX2, HLA-A, IFIT3, OASL, HLA-G, MX1, and IRF1. The at least 6 genes can include HLA-A, HLA-B, HLA-C, HLA-E, HLA-G, IFI27, IFI35, IFI6, IFIT1, IFIT3, IRF1, IRF2, IRF9, ISG15, MX1, MX2, OAS1, OAS2, OAS3, OASL, SOCS1, and STAT2. The at least 6 genes can include at least one of HLA-G, OAS1, OAS3, or SOCS1. The at least 6 genes can include at least two of HLA-G, OAS1, OAS3, or SOCS1. The at least 6 genes can include at least three of HLA-G, OAS1, OAS3, or SOCS1. The at least 6 genes can include HLA-G, OAS1, OAS3, and SOCS1. The method can comprise administering, after administering the one or more immunomodulatory agents, an oncolytic virus to the mammal.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 2. MV receptor transcripts in the primary GBM cell lines at baseline level (Next generation (Next-Gen) sequencing analysis) presented in reads-per-kilobase-per-million (RPKM) for the individual MV receptor genes SLAM, CD46 and nectin-4.

ns, not significant; statistical analysis two-tailed student t-test; *p<0.05; **p<0.01. Data are presented as the mean+/−s.e.m.

Figure 4:
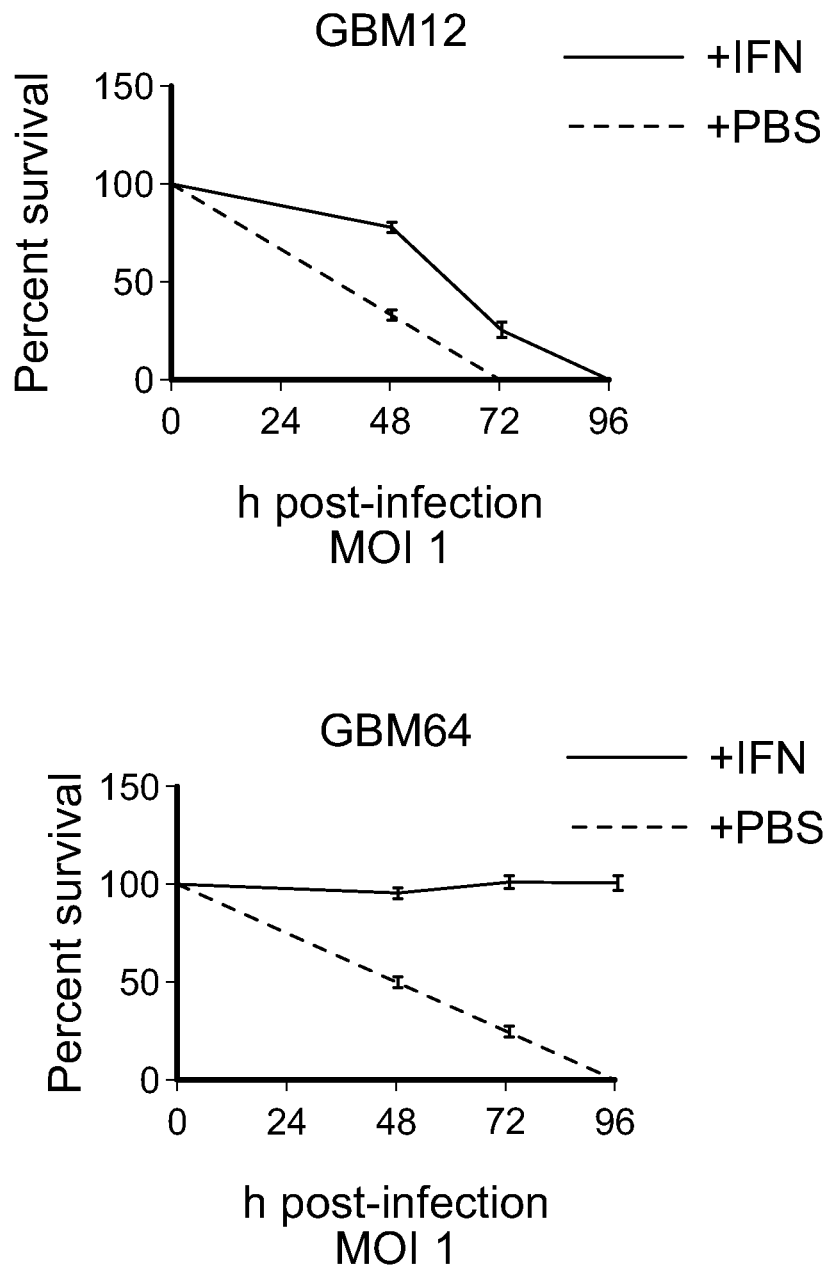

FIG. 4. MV permissive cells pre-treated with IFN leads to MV resistance. MV permissive GBM12 and 64 cells were pre-treated with recombinant human IFN-β (50 U/ml) for 18-24 hours prior to infection with MV-NIS (MOI 1) (n=3). Cell killing measured by MTT assay demonstrated that IFN-β treatment decreased the cell killing ability of MV. Data are mean+/−s.e.m.

FIG. 5. DLDA using the interferon gene signature predicts response to MV therapy in GBM and OvCa lines in vitro and in vivo. (a) Expression of the 22-gene signature was analyzed and illustrated in a heat-map consisting of 35 primary GBM lines (predicted responders and non-responders are indicated by a gray or black bar respectively). (b) Representative lines classified as permissive (GBM10) or resistant (GBM76), based on the DLDA analysis, were infected with MV-NIS (MOI 0.1) and virus production measured by titration on Vero cells 24-96 hours post-infection (n=3). Virus production in GBM10 cells was significantly greater than GBM76 cells (p-value<0.05). (c,d) GBM10 and GBM76 cells were infected with MV-NIS (MOI 1.0 and 0.1) and cell viability measured by MTT assay (n=3). GBM10 cells were effectively killed by MV, whereas more than 50% of cells remained viable following MV infection. (e,f) Athymic nude mice were implanted orthotopically with either GBM10 or GBM76 cells (n=10). Mice were treated with MV-NIS ($1 \times 10^5$ TCID$_{50}$/ml) once every 3 days for a total of 3 (GBM10) or 5 (GBM76) doses. MV therapy significantly improved median survival by 15 days (p-value<0.0001) in mice implanted with GBM10; whereas median survival in mice implanted with GBM76 cells was not improved (85 vs 89 days, p-value 0.1324). (g) Constitutive ISG expression was elevated in approximately 27% of the primary OvCa samples tested (23 out of 86). (h) Low ISG expressing OvCa line, PH077, and (i) a high ISG expressing line, PH080, were implanted intraperitoneally in SCID beige mice (10 mice/group). MV therapy significantly improved median survival 22 days in PH077 mice (p-value=0.0098); however, no benefit was measured in mice implanted with the high ISG expressing PH080 OvCa cells. ND, not detectable; ns, not significant; statistical analysis two-tailed student t-test; *p<0.05; **p<0.01. Data are presented as the mean+/−s.e.m.

FIG. 6. Expression of the interferon gene signature is inversely correlated with MV replication in MV treated GBM patients. (a) GBM patients were treated with MV-CEA ($2 \times 10^6$ patients 1-3 or $2 \times 10^7$ TCID$_{50}$ for patients 4-10) on day 0 and tumors resected on day 5. RNA was extracted from multiple regions of the treated tumors and virus replication was assessed by qRT-PCR for viral genome copies. (b) RNA was extracted from the primary tumors of GBM patients scheduled to receive MV therapy in an ongoing phase I trial. Gene expression was assessed by Nanostring analysis using a custom gene panel. Similar expression levels for the MV entry receptors are shown among patients. (c) Expression of the 22 ISG panel is depicted in the heat-map. The DLDA scoring system was applied to the patients, and classification assigned to each individual patient (black bar=resistant, gray bar=permissive). (d) DLDA scores calculated for each patient are inversely correlated to virus replication measured from the treated tumors, whereby elevated levels of ISG expression correlate with low levels of virus replication (p=−0.717; p-value=0.0297).

FIG. 7. Inhibition of the JAK/STAT pathway reduces the baseline level of interferon activation and sensitizes resistant cells to MV killing. (a) Resistant GBM39 cells were treated with the JAK1 inhibitor Ruxolitinib (Jakafi) (at 3 µM final concentration) or DMSO for 48 h prior to infection. Treated cells were infected with MV-NIS (MOI 0.1) and virus production measured 48, 72 and 96 h post-infection (n=3). (b) MV mediated cell killing was assessed in GBM39 cells pretreated with Jakafi (3 µM) or DMSO control by MTT cell viability assay (n=3). Pretreatment with Jakafi increased MV mediated cell killing in GBM39 cells. (c-g) RNA was extracted from GBM39 cells under the indicated conditions and ISG expression was assessed by qRT-PCR (n=2, run in technical triplicates). Pre-treatment with Jakafi decreased baseline ISG expression, as well as ISG induction upon MV infection. (h) Protein was extracted from GBM39 cells and (i) GBM12 cells under the indicated conditions and p-STAT1/3 activation measured by immunoblot. Constitutive activation of STAT3 was detected in uninfected GBM39 cells, as well as further STAT3 activation upon infection, both of which are blocked upon Jakafi treatment. Additionally, STAT1 was activated upon MV infection, which was blocked with Jakafi treatment. A similar, but delayed response was observed in GBM12 cells. (j) Jakafi (3 µM) was added at different points during the course of infection (MOI 0.1) and virus production was assessed 48 hours post-infection (n=3). Jakafi can be added up to 12 hours post-infection to sensitize resistant cells to MV infection. ND, not detectable; ns, not significant; statistical analysis two-tailed student t-test; *p<0.05; **p<0.01. Data are presented as the mean+/−s.e.m.

FIG. 8. JAK/STAT1 inhibition overcomes resistance in multiple primary GBM lines. GBM cells were treated with 3 µM Jakafi/DMSO for 48 hours prior to infection and virus production measured 48 hours post-infection (n=3). (a) Virus production in MV resistant cells was significantly increased in GBM76 and GBM6 cells. (b) Treatment with Jakafi further increased virus production in MV permissive cells. ND, not detectable; ns, not significant; statistical analysis two-tailed student t-test; *p<0.05; **p<0.01. Data are presented as the mean+/−s.e.m.

FIG. 9. A recombinant MV encoding the wild-type phosphoprotein (MV-P(wt)) circumvents IFN pathway activation. (a) RNA was isolated from uninfected GBM39 cells and cells infected with MV-GFP or MV-P(wt) (MOI 5) 12 hours post-infection. Expression of markers for the IFN pathway (RSAD2, OAS2, SAMD9, MX2 and MX1) was measured by qRT-PCR. ISG expression was significantly decreased in cells infected with MV-P(wt) relative to infection with MV-GFP (n=3). (b) Virus production was measured in GBM39 cells infected with MV-GFP or MV-P(wt) (MOI 0.1) at 48 and 72 hours post-infection (n=3). Virus production in MV-P(wt) infected cells reached levels 2-log greater than MV-GFP infected cells (p-value<0.05). ns, not significant; statistical analysis two-tailed student t-test; *p<0.05; **p<0.01. Data are presented as the mean+/−s.e.m.

Figure 10A:
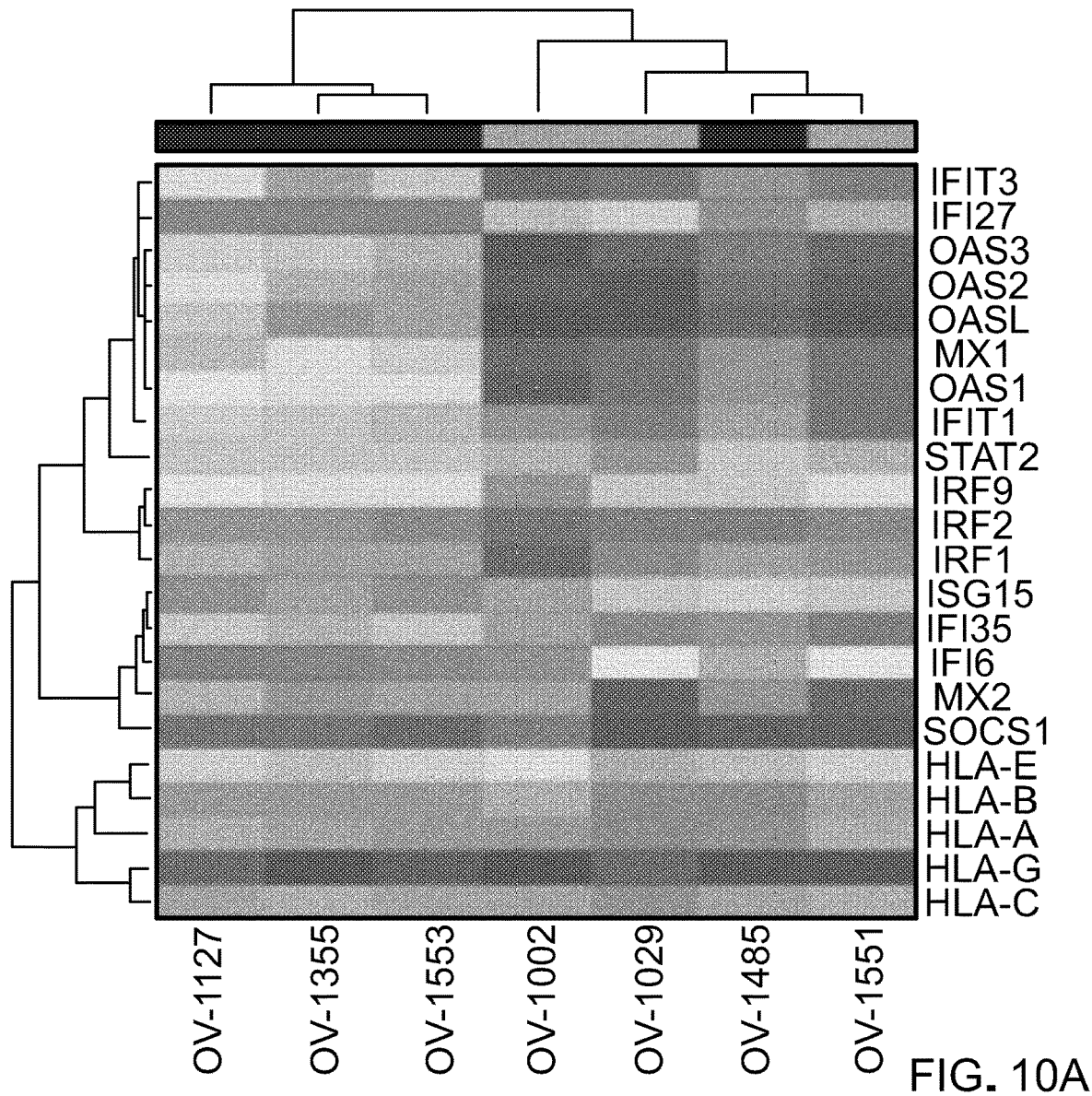

FIG. 10. MV treated OvCa patient's tumors are in a pre-existing antiviral state. (a) RNA was isolated from bulk frozen tumor tissue collected at the time of primary surgery. Gene expression was measured by RNA-Seq and expression of our gene signature is represented in the heat-map. DLDA scores for each patient were calculated based on our custom gene panel. 3 of the 7 patients were predicted to be responders (gray bar), while the remaining 4 patients were predicted to be non-responders (black bar). (b) Virus dose, DLDA score, prediction results and progression-free survival are presented. *patient removed from study due to abdominal infection, unrelated to therapy.

Figures 10B, 11:
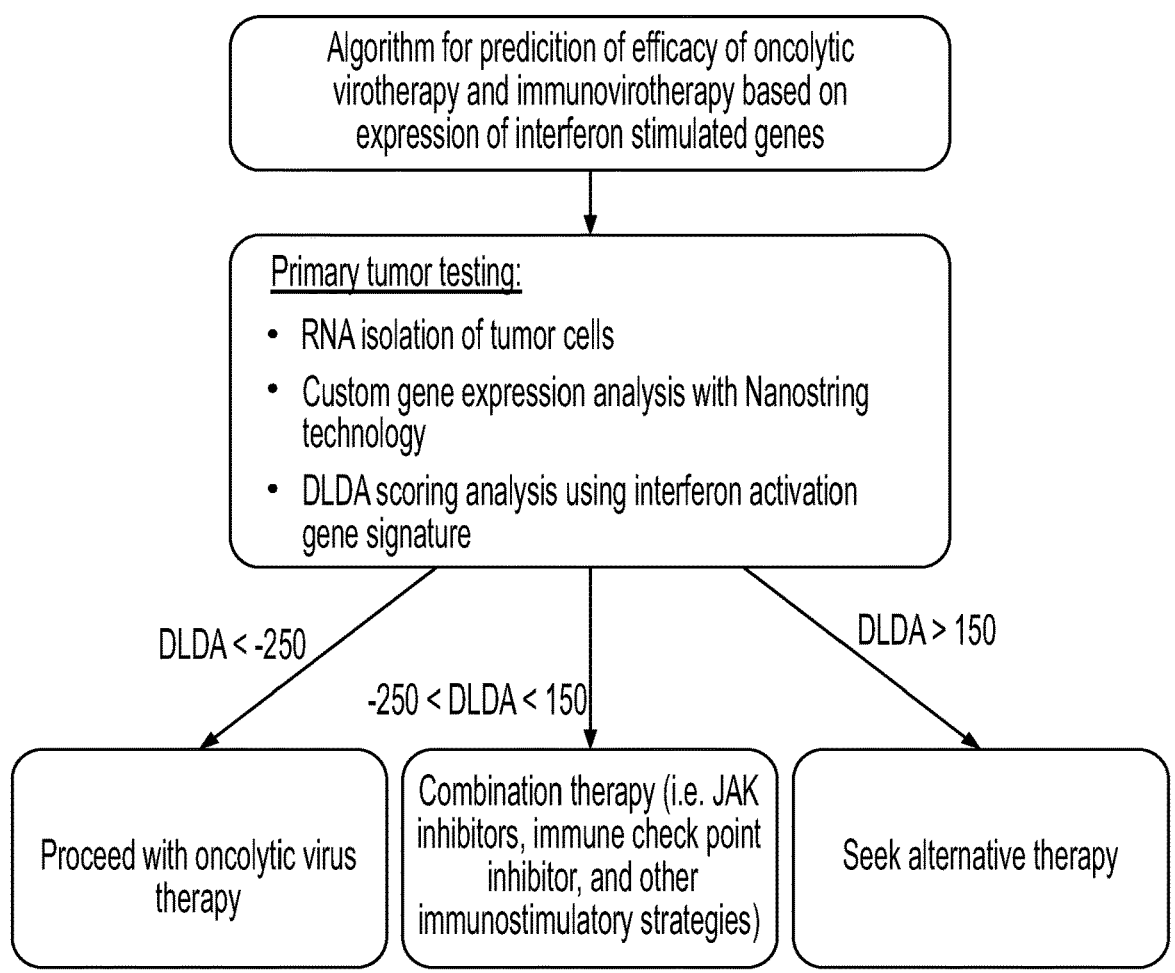

FIG. 11 is a diagram showing the use of DLDA with an ISG signatures in tumors to predict efficacy of virotherapy and immunovirotherapy, and select appropriate therapies.

DETAILED DESCRIPTION

This document provides materials and methods for treating cancer. In some cases, this document provides methods and materials for (a) identifying a mammal as having cancer cells responsive to treatment with one or more oncolytic viruses and (b) administering one or more oncolytic viruses (e.g., one or more oncolytic viruses) to treat the mammal. This document also provides materials and methods for determining the virotherapy responsiveness of cancer cells. For example, cancer cells obtained from a mammal having cancer can be assessed to determine if they are responsive or resistant to virotherapy based, at least in part, on a virotherapy permissive score (e.g., DLDA score), which is based, at least in part, on the ISG signature in a cancer cell.

Any appropriate mammal having cancer can be treated as described herein. For example, humans and other primates such as monkeys having cancer can be assessed for virotherapy responsiveness, and treated with one or more oncolytic viruses, and, optionally, one or more immunomodulatory agents, to reduce the number of cancer cells present within the human or other primate. In some cases, dogs, cats, horses, cows, pigs, sheep, mice, and rats can be assessed for virotherapy responsiveness, and treated with one or more oncolytic viruses as described herein.

Cancer cells from any appropriate cancer can be assessed for virotherapy responsiveness and, if responsive, the cancer can be treated with one or more oncolytic viruses, treated as described herein. For example, cancer cells from brain/CNS tumors (e.g., GBM), OvCa, head and neck cancers, sarcoma, mesothelioma, melanoma, colorectal cancer, breast cancer, lung cancer, prostate cancer, leukemia, or lymphoma can be assessed for virotherapy responsiveness, and, if responsive, the cancer can be treated with one or more oncolytic viruses, and, optionally, one or more immunomodulatory agents, as described herein. In some cases, cancer cells from a GBM can be assessed for virotherapy responsiveness, and, if responsive, the GBM can be treated with one or more oncolytic viruses, and, optionally, one or more immunomodulatory agents, as described herein. In some cases, cancer cells from an OvCa can be assessed for virotherapy responsiveness, and, if responsive, the OvCa can be treated with one or more oncolytic viruses, and, optionally, one or more immunomodulatory agents, as described herein.

Any appropriate method can be used to identify a mammal having cancer. For example, imaging techniques and biopsy techniques can be used to identify mammals (e.g., humans) having cancer.

Once identified as having cancer, the mammal can be assessed to determine whether or not the cancer will respond to treatment with one or more oncolytic viruses. For example, cancer cells obtained from the mammal having cancer can be assessed for virotherapy responsiveness. As described herein, RNA-Seq data sets from cancer cells (e.g., primary human GBM lines with known responses to MV therapy) can be used to determine a MV permissive score based, at least in part, on expression of an ISG signature (or an ISG expression profile) to determine virotherapy responsiveness. In some cases, an ISG signature can be applied to DLDA to obtain a DLDA score that can determine the response to treatment with one or more oncolytic viruses before administering the oncolytic viruses.

Any appropriate method can be used to identify the virotherapy permissive score (e.g., DLDA score) of cancer cells (e.g., cancer cells obtained from a mammal having cancer). The DLDA score of cancer cells can be obtained as described in the Examples and/or as described elsewhere (e.g., Dudoit et al., *Journal of the American Statistical Association* 97:77-87 (2002)). In some cases, DLDA scores for prospective samples are calculated based on several tumor (cancer) lines with known responses to virotherapy as a reference. For example, the DLDA score for cancer cells can be obtained by the following steps:

1) Obtain a gene expression value (e.g., the RPKM or transcript counts as obtained using, for example, RNA-Seq or Nanostring, respectively) for each ISG in an ISG signature. In general, one of the polypeptides typically secreted by virus-infected cells is IFN-β. Typically, IFN binding to the IFN receptor on infected and neighboring uninfected cells induces an antiviral state, which is characterized by the expression of more than 300 ISGs. Examples of ISGs that can be used in an ISG signature described herein include, without limitation, the genes set forth in Table 1.

TABLE 1

Interferon stimulated genes.

| Gene Signature | Chromosome location | Protein function |
| --- | --- | --- |
| OAS2 | 12 | Anti-viral |
| OAS1 | 12 | Anti-viral |
| IFI6 | 1 | Anti-viral |
| HLA-C | 6 | Peptide antigen binding |
| IFIT1 | 10 | Anti-viral |
| MX2 | 21 | Anti-viral |
| HLA-A | 6 | Peptide antigen binding |
| IFIT3 | 10 | Anti-viral |
| OASL | 12 | Anti-viral |
| HLA-G | 6 | Peptide antigen binding |
| MX1 | 21 | Anti-viral |
| IRF1 | 11 | Transcription factor (anti-viral) |
| SOCS1 | 16 | Cytokine regulation |
| ISG15 | 1 | Anti-viral |
| IFI27 | 14 | Anti-viral |
| IFI35 | 11 | Anti-viral |
| HLA-B | 6 | Peptide antigen binding |
| OAS3 | 12 | Anti-viral |
| HLA-E | 6 | MHC Class I binding |
| IRF9 | 14 | Transcription factor (anti-viral) |
| IRF2 | 8 | Transcription factor (anti-viral) |
| STAT2 | 10 | Transcription factor (anti-viral) |

Any appropriate methods can be used to identify a gene expression value. For example, mRNA-based assays such as RT-PCR (e.g., quantitative RT-PCR), RNA capture array, Nanostring analysis, and RNA sequencing (RNA-Seq) techniques can be used to determine if cancer cells have increased or decreased expression levels of ISGs as compared to those expression levels observed in control cells (e.g., cells with a known response to virotherapy therapy such as MV therapy). Examples of control cells include cells (e.g., GBM cells) with a known response to MV therapy. In some cases, control cells can include cancer cells known to be virotherapy permissive. For example, control cells can include GBM cells known to be MV permissive. In some cases, control cells include cancer cells known to be virotherapy resistant. For example, control cells can include GBM cells known to be MV resistant.

In some cases, an ISG signature used to obtain a virotherapy permissive score can be referred to as virotherapy permissive ISG signature. A virotherapy permissive ISG signature is an ISG signature that indicates that cancer cells (e.g., cells collected from a mammal having cancer) have significantly decreased expression levels of ISGs as compared to those expression levels observed in control cells (e.g., cells permissive to virotherapy therapy such as MV therapy). For example, an ISG signature having a statistically significant decrease in expression of each ISG in the ISG signature relative to the expression levels observed in control cells (e.g., cells permissive to virotherapy therapy such as MV therapy) can be used to assess virotherapy responsiveness. In some cases, an ISG signature can include at least 5 (e.g., at least 6, at least 7, at least 8, at least 9, at least 10, at least 11, or at least 12) ISGs set forth in Table 1. For example, an ISG signature can include about 5 ISGs to about 22 ISGs (e.g., about 6 ISGs to about 20 ISGs, about 6 ISGs to about 18 ISGs, about 6 ISGs to about 15 ISGs, about 6 ISGs to about 12 ISGs, about 8 ISGs to about 22 ISGs, about 10 ISGs to about 22 ISGs, or about 12 ISGs to about 22 ISGs). In some cases, an ISG signature can include 6 ISGs (e.g., OAS2, OAS1, IFI6, HLA-C, IFIT1, and MX2). In some cases, an ISG signature can include 12 ISGs (e.g., OAS2, OAS1, IFI6, HLA-C, IFIT1, MX2, HLA-A, IFIT3, OASL, HLA-G, MX1, and IRF1). In some cases, an ISG signature can include the 22 ISGs set forth in Table 1 (i.e., HLA-A, HLA-B, HLA-C, HLA-E, HLA-G, IFI27, IFI35, IFI6, IFIT1, IFIT3, IRF1, IRF2, IRF9, ISG15, MX1, MX2, OAS1, OAS2, OAS3, OASL, SOCS1, and STAT2).

In some cases, a gene expression value (e.g., the RPKM or transcript counts as obtained using, for example, RN-Seq or Nanostring, respectively) also can be obtained for genes commonly expressed in one or more virotherapy permissive cell lines (e.g., GBM43 and GBM64) and in one or more virotherapy resistant cell lines (e.g., GBM39, GBM6 and GBM150). In some cases, genes commonly expressed in both a virotherapy permissive cell and a virotherapy resistant cell can include genes set forth in Appendix A. For example, gene expression values can be obtained for each of the 790 genes set forth in Appendix A. The gene expression values for genes commonly expressed in both a virotherapy permissive cell and a virotherapy resistant cell can be used to establish the standardized ISG expression values for the ISG in an ISG signature as described herein (see, e.g., Example 1).

2) Transform the gene expression values. Each gene expression value can be transformed by adding the value of 1.0 to each gene expression value, and then log 2 transforming each gene expression value. The within-sample mean and standard deviation based on the log 2-transformed gene expression values can be calculated, and the mean subtracted from the log 2-transformed gene expression values. The results are then divided by the within-sample standard deviation.

3) Calculate the total ISG expression value. The transformed expression value for each ISG in an ISG signature is then multiplied by an ISG coefficient such as those set forth in Table 2A or an ISG coefficient within a range set forth in Table 2B.

TABLE 2A

ISG-DLDA Coefficients.

| | Coefficient | | |
| --- | --- | --- | --- |
| ISG Gene Symbol | 22 ISG signature | 12 ISG signature | 6 ISG signature |
| HLA-A | 34.35067 | 34.35067 | 0 |
| HLA-B | 16.63304 | 0 | 0 |
| HLA-C | 80.03653 | 80.03653 | 80.03653 |
| HLA-E | 7.939461 | 0 | 0 |
| HLA-G | 20.69257 | 20.69257 | 0 |
| IFI27 | 2.801251 | 0 | 0 |
| IFI35 | 7.915572 | 0 | 0 |
| IFI6 | 47.07211 | 47.07211 | 47.07211 |
| IFIT1 | 42.98597 | 42.98597 | 42.98597 |
| IFIT3 | 18.71784 | 18.71784 | 0 |
| IRF1 | 22.62736 | 22.62736 | 0 |
| IRF2 | 8.269744 | 0 | 0 |
| IRF9 | 6.019136 | 0 | 0 |
| ISG15 | 67.27749 | 0 | 0 |
| MX1 | 58.9203 | 58.9203 | 0 |
| MX2 | 65.90186 | 65.90186 | 65.90186 |
| OAS1 | 311.1704 | 311.1704 | 311.1704 |
| OAS2 | 222.1048 | 222.1048 | 222.1048 |
| OAS3 | 5.651453 | 0 | 0 |
| OASL | 15.91084 | 15.91084 | 0 |
| SOCS1 | 16.0131 | 16.0131 | 0 |
| STAT2 | −1.11101 | 0 | 0 |

TABLE 2B

ISG-DLDA Coefficient Ranges.

| | Coefficient Ranges | | | | | |
| --- | --- | --- | --- | --- | --- | --- |
| ISG Gene | 22 ISG signature | | 12 ISG signature | | 6 ISG signature | |
| Symbol | min. | max. | min. | max. | min. | max. |
| HLA-A | 17.17534 | 51.52601 | 17.17534 | 51.52601 | 0 | 0 |
| HLA-B | 8.316522 | 24.94957 | 0 | 0 | 0 | 0 |
| HLA-C | 40.01826 | 120.0548 | 40.01826 | 120.0548 | 40.01826 | 120.0548 |
| HLA-E | 3.969731 | 11.90919 | 0 | 0 | 0 | 0 |
| HLA-G | 10.34628 | 31.03885 | 10.34628 | 31.03885 | 0 | 0 |
| IFI27 | 1.400625 | 4.201876 | 0 | 0 | 0 | 0 |
| IFI35 | 3.957786 | 11.87336 | 0 | 0 | 0 | 0 |
| IFI6 | 23.53606 | 70.60817 | 23.53606 | 70.60817 | 23.53606 | 70.60817 |
| IFIT1 | 21.49299 | 64.47896 | 21.49299 | 64.47896 | 21.49299 | 64.47896 |
| IFIT3 | 9.35892 | 28.07676 | 9.35892 | 28.07676 | 0 | 0 |
| IRF1 | 11.31368 | 33.94104 | 11.31368 | 33.94104 | 0 | 0 |
| IRF2 | 4.134872 | 12.40462 | 0 | 0 | 0 | 0 |
| IRF9 | 3.009568 | 9.028704 | 0 | 0 | 0 | 0 |
| ISG15 | 33.63874 | 100.9162 | 0 | 0 | 0 | 0 |
| MX1 | 29.46015 | 88.38045 | 29.46015 | 88.38045 | 0 | 0 |

TABLE 2B-continued

ISG-DLDA Coefficient Ranges.

| ISG Gene Symbol | 22 ISG signature | | 12 ISG signature | | 6 ISG signature | |
|---|---|---|---|---|---|---|
| | min. | max. | min. | max. | min. | max. |
| MX2 | 32.95093 | 98.85279 | 32.95093 | 98.85279 | 32.95093 | 98.85279 |
| OAS1 | 155.5852 | 466.7556 | 155.5852 | 466.7556 | 155.5852 | 466.7556 |
| OAS2 | 111.0524 | 333.1572 | 111.0524 | 333.1572 | 111.0524 | 333.1572 |
| OAS3 | 2.825727 | 8.47718 | 0 | 0 | 0 | 0 |
| OASL | 7.95542 | 23.86626 | 7.95542 | 23.86626 | 0 | 0 |
| SOCS1 | 8.006551 | 24.01965 | 8.006551 | 24.01965 | 0 | 0 |
| STAT2 | −0.55551 | −1.66652 | 0 | 0 | 0 | 0 |

The results for each ISG in an ISG signature multiplied by the appropriate coefficient as set forth in Table 2A or 2B are added together to obtain a total ISG expression value. For example, when an ISG signature contains 22 ISGs, the total ISG expression value is the sum of the transformed gene expression value multiplied by the appropriate coefficient of those 22 ISGs. For example, when an ISG signature contains 12 ISGs, the total ISG expression value is the sum of the transformed gene expression value multiplied by the appropriate coefficient of those 12 ISGs. For example, when an ISG signature contains 6 ISGs, the total ISG expression value is the sum of the transformed gene expression value multiplied by the appropriate coefficient of those 6 ISGs.

3) Calculate the DLDA score. An ISG-DLDA model constant (see, e.g., Table 5) is subtracted from the total ISG expression value. In some cases, the ISG-DLDA model constant subtracted from the ISG expression value can be adjusted based upon the number of ISGs in the ISG signature. For example, when an ISG signature contains 22 ISGs, 670.61 is subtracted from the total ISG expression value to obtain the DLDA score. For example, when an ISG signature contains 12 ISGs, 503.76 is subtracted from the total ISG expression value to obtain the DLDA score. For example, when an ISG signature contains 6 ISGs, 384.89 is subtracted from the total ISG expression value to obtain the DLDA score.

Once the DLDA score for cancer cells (e.g., cancer cells obtained from a mammal having cancer) has been obtained, the cancer can be assessed to determine virotherapy responsiveness of the cancer, and to select a treatment option for the mammal.

The thresholds for converting the DLDA scores into virotherapy permissive or virotherapy resistant scores can vary based upon the number of ISGs in the ISG signature as shown in Table 3. For example, when an ISG signature contains 22 ISGs, the DLDA score thresholds can be between about −250 and about 150. For example, when an ISG signature contains 12 ISGs, the DLDA score thresholds can be between about −150 and about 200. For example, when an ISG signature contains 6 ISGs, the DLDA score thresholds can be between about −150 and about 150. In some cases, if cancer cells (e.g., cancer cells obtained from a mammal having cancer) are identified as having a low or intermediate DLDA score, then the cancer can be classified as having a cancer responsive to treatment with one or more oncolytic viruses effective to kill cancer cells via viral replication. For example, when cancer cells are identified as having a low DLDA score (e.g., less than −250 based on an ISG signature having 22 ISGs), then the cancer can be classified as having a cancer responsive to treatment with one or more oncolytic viruses as the sole anti-cancer treatment agent. For example, when cancer cells are identified as having an intermediate DLDA score (e.g., about −250 to about 150 based on an ISG signature having 22 ISGs), then the cancer can be classified as having a cancer that is responsive to treatment with one or more oncolytic viruses in combination with one or more immunomodulatory agents. In some cases, if cancer cells (e.g., cancer cells obtained from a mammal having cancer) are identified as having a high DLDA score, then the cancer can be classified as having a cancer resistant to treatment with one or more oncolytic viruses effective to kill cancer cells via viral replication. For example, when cancer cells are identified as having a DLDA score greater than 150, based on an ISG signature having 22 ISGs, then the cancer can be classified as having a cancer that is resistant to treatment with an oncolytic virus. In some cases, the DLDA score for cancer cells can be used to select a treatment options as set forth in Table 3.

TABLE 3

Treatment options.

| | DLDA score | | | |
|---|---|---|---|---|
| virotherapy permissive score | 22 ISG signature | 12 ISG signature | 6 ISG signature | Treatment regimen |
| low | <−250 | <−150 | | Treat with oncolytic virus(es) |
| intermediate | −250 > x < 150 | −150 > x < 200 | −150 > x < 150 | Treat with oncolytic virus(es) and immunomodulatory agent(s) |

TABLE 3-continued

Treatment options.

| | DLDA score | | | |
|---|---|---|---|---|
| | 22 ISG signature | 12 ISG signature | 6 ISG signature | Treatment regimen |
| virotherapy resistant score | | | | |
| high | >150 | >200 | >150 | Patients should not receive oncolytic therapy; alternative approaches should be used (surgery, chemotherapy, etc.) |

When a mammal is identified as having cancer cells that are responsive to treatment with one or more oncolytic viruses based, at least in part, on having a low DLDA score, the mammal can be administered or instructed to self-administer one or more oncolytic viruses to reduce the number of cancer cells present within the mammal. In some cases, an oncolytic virus can be a replication-competent oncolytic virus, a conditionally replicating virus vector, or a non-replicating virus vector. Examples of oncolytic viruses include, without limitation, MV, Vesicular stomatitis virus (VSV), Newcastle disease virus (NDV), vaccinia, replication competent retroviruses, herpes simplex virus, myxoma virus, adenovirus, adeno-associated virus, and reovirus. In some cases, an oncolytic virus is not detected and/or destroyed by the immune system (e.g., the immune system of mammal that the oncolytic virus is administered to). For example, an oncolytic virus can encode a polypeptide (e.g., modified self-protein or a transgene) that can help evade innate immune system detection. In some cases, a mammal having cancer cells that are responsive to treatment with one or more oncolytic viruses can be administered or instructed to self-administer a MV to reduce the number of cancer cells present within the mammal. In some cases, two or more oncolytic viruses (e.g., two, three, four, five, or more oncolytic viruses) described herein can be administered to a mammal to reduce the number of cancer cells present within the mammal.

When a mammal is identified as having cancer cells that are responsive to treatment with one or more oncolytic viruses based, at least in part, on having cancer cells with an intermediate DLDA score, the mammal can be administered or instructed to self-administer one or more oncolytic viruses (e.g., MV) in combination with one or more immunomodulatory agents (e.g., JAK/Stat inhibitors and/or immune checkpoint inhibitors) to reduce the number of cancer cells present within the mammal. Examples of immunomodulatory agents include, without limitation, JAK1 inhibitors (e.g., ruxolitinib (Jakafi)), anti-PD1 antibodies (e.g., pembrolizumab or nivolumab), anti-PDL1 antibodies (e.g., atezolizumab or durvalumab), anti-CTLA4 antibodies (e.g., ipilimumab), and vector expressed immunomodulatory transgenes. In some cases, a mammal having cancer cells that are responsive to treatment with one or more oncolytic viruses based, at least in part, on having cancer cells with an intermediate DLDA score, can be administered or instructed to self-administer a MV and ruxolitinib to reduce the number of cancer cells present within the mammal. In some cases, two or more oncolytic viruses (e.g., two, three, four, five, or more oncolytic viruses) and two or more immunomodulatory agents can be administered to a mammal to reduce the number of cancer cells present within the mammal. In cases where one or more oncolytic viruses are used in combination with one or more immunomodulatory agents to treat cancer, the one or more immunomodulatory agents can be administered at the same time or independently of the administration of one or more oncolytic viruses. For example, the composition including one or more oncolytic viruses can be administered before, during, or after the one or more immunomodulatory agents are administered.

When a mammal is identified as having cancer cells that are resistant to treatment with one or more oncolytic viruses (e.g., having cancer cells with a high DLDA score), the mammal can be administered or instructed to self-administer one or more alternative cancer treatments to reduce the number of cancer cells present within the mammal. Examples of alternative cancer treatments include, without limitation, surgery, chemotherapy, and radiation.

In some cases, one or more oncolytic viruses, and, optionally, one or more immunomodulatory agents, can be administered to a mammal once or multiple times over a period of time ranging from days to weeks. In some cases, one or more oncolytic viruses, and, optionally, one or more immunomodulatory agents, can be formulated into a pharmaceutically acceptable composition for administration to a mammal having cancer. For example, a therapeutically effective amount of a MV, and, optionally, ruxolitinib, can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more oncolytic viruses, and, optionally, one or more immunomodulatory agents, can be designed for oral, parenteral (including subcutaneous, intramuscular, intravenous, and intradermal), or intratumoral administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition including one or more oncolytic viruses, and, optionally, one or more immunomodulatory agents, can be administered locally (e.g., intratumorally) or systemically. For example, a composition provided herein can be administered locally by injection into tumors or into biological spaces infiltrated by tumors (e.g. peritoneal cavity and/or pleural space). In some cases, a composition provided herein can be administered systemically, orally, or by injection to a mammal (e.g., a human).

Effective doses can vary depending on the severity of the cancer, the route of administration, the age and general health condition of the subject, excipient usage, the possibility of co-usage with other therapeutic treatments such as use of other agents, and the judgment of the treating physician.

An effective amount of a composition containing one or more oncolytic viruses, and, optionally, one or more immunomodulatory agents, can be any amount that reduces the number of cancer cells present within the mammal without producing significant toxicity to the mammal. For example, an effective amount of an oncolytic virus (e.g., MV) can be from about $1\times10^3$ $TCID_{50}$ (tissue culture infective dose) per dose to about $1\times10^9$ $TCID_{50}$ per dose (e.g., from about $1\times10^4$ $TCID_{50}$ per dose to about $1\times10^9$ $TCID_{50}$ per dose, from about $1\times10^5$ $TCID_{50}$ per dose to about $1\times10^9$ $TCID_{50}$ per dose, from about $1\times10^6$ $TCID_{50}$ per dose to about $1\times10^9$ $TCID_{50}$ per dose, from about $1\times10^7$ $TCID_{50}$ per dose to about $1\times10^9$ $TCID_{50}$ per dose, from about $1\times10^8$ $TCID_{50}$ per dose to about $1\times10^9$ $TCID_{50}$ per dose, from about $1\times10^3$ $TCID_{50}$ per dose to about $1\times10^8$ $TCID_{50}$ per dose, from about $1\times10^3$ $TCID_{50}$ per dose to about $1\times10^7$ $TCID_{50}$ per dose, from about $1\times10^3$ $TCID_{50}$ per dose to about $1\times10^6$ $TCID_{50}$ per dose, from about $1\times10^3$ $TCID_{50}$ per dose to about $1\times10^5$ $TCID_{50}$ per dose, from about $1\times10^3$ $TCID_{50}$ per dose to about $1\times10^4$ $TCID_{50}$ per dose, from about $1\times10^4$ $TCID_{50}$ per dose to about $1\times10^8$ $TCID_{50}$ per dose, or from about $1\times10^5$ $TCID_{50}$ per dose to about $1\times10^7$ $TCID_{50}$ per dose). In some cases, from about $1\times10^6$ $TCID_{50}$ to about $1\times10^9$ $TCID_{50}$ (e.g., from about $1\times10^7$ $TCID_{50}$ to about $1\times10^9$ $TCID_{50}$, from about $1\times10^8$ $TCID_{50}$ to about $1\times10^9$ $TCID_{50}$, from about $1\times10^6$ $TCID_{50}$ to about $1\times10^8$ $TCID_{50}$, or from about $1\times10^6$ $TCID_{50}$ to about $1\times10^7$ $TCID_{50}$) of an oncolytic virus such as MV can be administered to a human (e.g., directly into a tumor of a human) as the sole anti-cancer treatment agent. In some cases, from about $1\times10^3$ $TCID_{50}$ to about $1\times10^6$ $TCID_{50}$ (e.g., from about $1\times10^4$ $TCID_{50}$ to about $1\times10^6$ $TCID_{50}$, from about $1\times10^5$ $TCID_{50}$ to about $1\times10^6$ $TCID_{50}$, from about $1\times10^3$ $TCID_{50}$ to about $1\times10^5$ $TCID_{50}$, or from about $1\times10^3$ $TCID_{50}$ to about $1\times10^5$ $TCID_{50}$) of an oncolytic virus such as MV can be administered to a human (e.g., directly into a tumor of a human) in combination with one or more immunomodulatory agents (e.g., JAK/Stat inhibitors and/or immune checkpoint inhibitors).

If a particular mammal fails to respond to a particular amount, then the amount of an oncolytic virus, and, optionally, one or more immunomodulatory agents, can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of an oncolytic virus, and, optionally, one or more immunomodulatory agents, can be any amount that reduces the number of cancer cells present within the mammal without producing significant toxicity to the mammal. For example, the frequency of administration of a MV, and, optionally, ruxolitinib, can be from about two to about three times a week to about two to about three times a month. In some cases, a mammal having cancer identified as having cancer cells responsive to one or more oncolytic viruses can receive a single administration of an oncolytic virus. The frequency of administration of an oncolytic virus, and, optionally, one or more immunomodulatory agents, can remain constant or can be variable during the duration of treatment. A course of treatment with a composition containing an oncolytic virus, and, optionally, one or more immunomodulatory agents, can include rest periods. For example, a composition containing one or more oncolytic viruses, and, optionally, one or more immunomodulatory agents, can be administered every other month over a two-year period followed by a six-month rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more oncolytic viruses, and, optionally, one or more immunomodulatory agents, can be any duration that reduces the number of cancer cells present within the mammal without producing significant toxicity to the mammal. In some cases, the effective duration can vary from several months to several years. In general, the effective duration for reducing the number of cancer cells present within the mammal can range in duration from about one or two months to five or more years. Multiple factors can influence the actual effective duration used for a particular treatment. For example, an effective duration can vary with the frequency of administration, effective amount, use of multiple treatment agents, route of administration, and severity of the condition being treated.

In certain instances, a course of treatment, the number of cancer cells present within a mammal, and/or the severity of one or more symptoms related to the condition being treated (e.g., cancer) can be monitored. Any appropriate method can be used to determine whether or not the number of cancer cells present within a mammal is reduced. For example, imaging techniques can be used to assess the number of cancer cells present within a mammal. For example, imaging reporters and/or biomarker reporter transgenes (e.g., vector-encoded reporter transgenes) can be used to monitor the efficiency of the virus infection and/or virus replication.

The invention will be further described in the following examples, which do not limit the scope of the invention described in the claims.

EXAMPLES

Example 1: Analysis of Cancer Cells Responsive to Oncolytic Virus Treatment

Materials and Methods

Cell Lines and Tissue Culture.

African green monkey Vero cells and human embryonic kidney 293 cells were purchased from the American Type Culture Collection (ATCC) and grown according to the ATCC recommendations (ATCC, Rockville, Md.). Primary cells were isolated from GBM patients who had tumor surgery at Mayo Clinic, Rochester Minn. (Gianinni et al. 2005 Neuro Oncol 7:164-176). Cells were maintained by passaging as xenograft tumors in mice. Primary cells were grown in DMEM (HyClone) supplemented with 10% fetal bovine serum (FBS) and antibiotics (Life Technologies).

MV Strains and Virus Propagation.

Generation and characterization of MV strains expressing human iodide symporter (MV-NIS), human carcinoembryonic antigen (MV-CEA) and green fluorescent protein (MV-GFP) has been described elsewhere (see, e.g., Dingli et al. 2004 Blood 103:1641-1646; Peng et al. 2002 Cancer Res 62:4656-4662; Duprex et al. 1999 J Virol 73:9568-9575). Viruses were propagated on Vero cells and viral stocks were prepared by repeated freezing-thawing and stored frozen at −80° C. MV titers were determined in tissue culture infectious doses 50% ($TCID_{50}$) per ml by titration on Vero cells described elsewhere (see, e.g., Iankov et al. 2009 Mol Ther 17:1395-1403). High grade purified viral stocks from supernatant released viruses were prepared as described elsewhere (see, e.g., Langfield et al. 2011 Methods Mol Biol 737:345-366).

MV Anti-Tumor Effect In Vitro.

GBM cells were inoculated at a multiplicity of infection (MOI) of 0.1 and 1.0 with MV strains diluted in Opti-MEM (Life Technologies). MTT proliferation assay (ATCC, Rockville, Md.) was used to determine the cell viability at 24 hours to 10 days post MV inoculation. Samples were run 6-8 wells in 96-well plates and cells inoculated with inactivated MV were used as control.

MV Growth Kinetics.

Growth kinetics of MV in primary GBM cells was determined by titration on Vero cells for the cell-associated virus at different time points post infection with MV-NIS. Briefly, the $4 \times 10^5$ cells were inoculated at a MOI of 0.1 with MV-NIS and incubated in 6-well cell culture plates (Falcon). Cells were harvested at 24, 48, 72 and 96 hours, freeze/thawed twice (to release the cell-associated virus) and centrifuged to remove the debris. Samples were then titrated by incubation of 10-fold sample dilutions in Opti-MEM were incubated on Vero cells in 96-well plates (Falcon). Wells positive for syncytia were counted at 72 hours and virus titers were calculated as described above.

Jakafi Treatments.

Jakafi (Selleck Chem.) was diluted in DMSO and used to treat GBM39 cells. Cells were treated with 3 µM of Jakafi 48 hours prior to infection, at the time of infection, 6 hours post-infection, or 12 hours post-infection. Infections were conducted in the presence of the drug throughout the experiment, unless indicated.

ELISA, SDS-PAGE and Immunoblotting.

For immunoblotting, cells were lysed in RIPA buffer (prepared according to Santa Cruz Biotechnology protocol) supplemented with Halt Phosphatase Inhibitor Cocktail (Fisher Pierce) and cOmplete protease inhibitor cocktail (Roche). Samples were mixed (undiluted or diluted in RIPA buffer) 1:1 vol./vol. with sample buffer (Bio-Rad). The proteins were resolved on 12.5% or 15% Criterion gels using Criterion electrophoresis system (Bio-Rad). Pre-stained proteins (Bio-Rad) were used as molecular weight (MW) markers. SDS-PAGE resolved proteins were then transferred to PVDF membranes (Bio-Rad) using semi-dry blotting system (Bio-Rad). Membranes were washed in phosphate-buffered saline (PBS) and blocked in 10% non-fat dry milk (Bio-Rad) in PBS with 0.05% Tween 20 (PBS/T). Membranes were incubated with MAbs, STAT1 (Santa Cuz Biotechnology), p-STAT1 (Cell Signaling Technology), STAT3 (Santa Cuz Biotechnology), p-STAT3 (Santa Cuz Biotechnology), and tubulin (Sigma) diluted in 1% non-fat milk in PBS/T and incubated for 2-4 hours at room temperature. Membranes were washed in PBS/T and incubated for 1-2 hours with horse-radish peroxidase (HRP) conjugated anti-mouse IgG antibody (Santa Cuz Biotechnology) or mouse specific polyvalent immunoglobulin (G, A, M) HRP conjugate (Sigma) secondary antibodies. Reaction was visualized by 1-2-minutes incubation with chemiluminescent substrate (Pierce).

Flow Cytometry.

Flow cytometry was utilized for detection of GFP positive cells.

Briefly, cells were infected with MV at MOI=1.0. Cells were collected at 24 hours and washed in PBS. The cells were fixed in 4% paraformaldehyde (Sigma) and analyzed for GFP expression by flow cytometry.

Immunohistochemistry (IHC).

For IHC, tumor samples collected from patients and xenograft tumors in mice were fixed in 10% formalin and paraffin embedded. Microscopic slides with 5-10 µm thick tissue sections were deparaffined using Citrysolv after antigen retrieval procedure were blocked with 10% serum in PBS. Slides were incubated with MAb 8A11 hybridoma supernatants (specific for MV nucleoprotein (N) protein) in dilution 1:10-50 for 2-4 hours at room temperature. After washing in PBS the slides were incubated with secondary HRP-conjugated antibody diluted 1:100 in PBS/10% serum for 2 hours. Then the slides were washed and incubated with DAB substrate according to the manufacturer's protocol (Vector). Hematoxylin was used for counterstaining.

Animal experiments.

Orthotopic GBM tumors were engrafted in female athymic nude mice (Harlan, Indianapolis Ind.). All animal experiments and in vivo procedures were approved by the Mayo Foundation Institutional Animal Care and Use Committee. In order to evaluate anti-tumor efficacy, exponentially grown $3 \times 10^5$ GBM-12, 10, 76 and GBM-39 cells were implanted in mice by stereotactic injection in caudate nucleus using a small animal stereotactic frame (Paraskevakou et al. 2007 Mol Ther 15:677-686). Mice were treated with 3 or 5 orthotopic injections of MV-NIS ($10^5$ $TCID_{50}$ per injection). Control groups received the same dose of inactivated viruses. Animals were monitored daily and were euthanized when developed neurological impairment or weigh loss>15% of the body weight. Low passage ovarian cancer PDX lines were established in 6-8 week old female SCID-beige mice (Harlan). Briefly, tumors were minced and mixed with McCoy's media (Media Tech) and approximately 0.3-0.5 cc of tumor injected intraperitoneally. Mice were randomized and treatment started when tumor area reached a pre-established size of 0.3-0.6 cm$^3$, as measured by ultrasound. Mice that did not have detectable tumors were excluded from the study. Mice received $1\times10^6$ TCID$_{50}$ MV-NIS or inactivated virus once per week for 3 weeks delivered intraperitoneally. Kaplan-Meyer survival curves were plotted and median survival of the animal groups was compared by the log-rank test on GraphPad Prism 5.0 software (GraphPad Software, San Diego, Calif.).

Patients and Patient Samples.

All studies involving patients were approved by the Mayo Clinic Institutional Review Board. Patients with recurrent GBM tumors were treated by stereotactic injection of MV-CEA in the ongoing phase I clinical trial at Mayo Clinic, Rochester Minn. Tumor tissues removed en bloc with a catheter tip in place were received in pathology, measured and photographed. Subsequently the catheter was removed and the fresh tissue was cut in serial sections (2-3 mm in thickness) perpendicularly to the catheter. Tissue was promptly frozen in liquid nitrogen and stored at −80 degrees.

Tumor tissue samples were collected from 5 patients by surgical resection performed on day 5 post MV treatment. Tumor tissue was sectioned and kept frozen at −80° C. or fixed in 10% formalin. Formalin-fixed/paraffin-embedded (FFPE) tumor tissue samples collected during the primary surgery were also used for the subsequent histological staining, IHC, quantitative RT-PCR and whole transcriptome analysis. Normal brain tissue collected after surgery was used as control.

Whole Transcriptome Sequencing Analyses.

Early in vivo passages of the primary GBM-12 and GBM-39 cells were infected with MOI=5.0 of MV-GFP for 12 hours. RNA was isolated and cDNA libraries of poly-A RNA or total RNA extracts were prepared and analyzed using Next-Gen sequencing (NGS) technology. The whole transcriptome (RNA-seq) was analyzed by aligning the sequences to human genome and MV genome at a base-level resolution. Transcript expression level in MV-infected cells was compared to the uninfected control cells. Baseline level (uninfected cells) and MV infection-triggered gene expression of GBM-39 (prototype of MV infection resistant cells) cells was compared to that of the GBM-12 cells (MV susceptible cell prototype). This comparison allowed identification of the genes potentially involved in restriction of MV infection and replication between MV susceptible and infection resistant GBM cells.

The total RNA from FFPE tissue samples collected following primary surgery of GBM patients was isolated by a laser-capture microdissection (LCM) technique using Arcturus Veritas System (Applied Biosystems). LCM was used to capture individual MV infected tumor cells detected by IHC on parallel tissue sections. Tumor samples were collected from the GBM patients at day 5 post MV treatment and tumor cells were harvested by LCM and subjected to NGS analysis. In addition, samples from treated patients were analyzed by IHC for expression of MV N protein as an evidence for virus infection within GBM cells. Then on parallel tissue sections MV-infected cells were LCM captured and their gene expression profile was analyzed as described above.

A cDNA library was prepared from a total RNA extract and analyzed using the NuGen technology (NuGEN Technologies) for sequencing of the whole transcriptome from fragmented RNA in FFPE specimens. The process of library preparation, NGS and data analysis was conducted in cooperation with the Medical Genome Facility and Biomedical Statistics at Mayo Clinic, Rochester Minn. The data were analyzed and expression values for each gene were normalized to 1 million reads and corrected for gene length (Reads Per/kilo base-pair per Million mapped reads, RPKM). Heatmap figures were generated using the enhanced heatmap function from the R library package 'gplots' (Langmead et al. 2009 *Genome Biol* 10:R25; Trapnell et al. 2009 *Nat Biotechnol* 27:455-457).

Gene expression data from GBM PDX data was obtained from a recently submitted study (ref. in prep from Sarkaria lab). Briefly, each PDX line was grown orthotopically and a single tumor-bearing brain was flash frozen in Optimal Cutting Temperature (OCT) medium (Tissue-Tek, Sakura FineTek USA Inc., Torrance, Calif.). RNA was isolated from tumor tissue that was scraped from multiple serial tumor sections. Total RNA (50 ng) of each sample was used to generate whole transcriptome libraries using Illumina's TruSeq RNA Sample Prep Kit V2 (Illumina) according to manufacturer's protocol. RNA-seq data from the PDX lines was processed using Map-RSeq, a Mayo Clinic developed bioinformatics pipeline for RNA sequencing. Sailfish was used to estimate isoform RPKM expression.

The total 86 fresh frozen ovarian tumor tissue were obtained from consenting patients at the time of surgery. RNA was simultaneously extracted following the manufacturers protocol by Qiagen RNeasy Mini Kit (#74104). Nucleic acid concentration was determined on a Thermo Scientific NanoDrop 2000c UV-Vis Spectrophotometer. All RINs were >7.0, as determined using the Agilent Bioanalyzer. The cDNA libraries were prepared from polyA enriched RNA using Illumina TruSeq v2 mRNA kit (#RS-122). cDNA fragments of 300-400 bp were selected, and non-directional 50 nucleotide paired-end sequencing was performed. Sequencing was carried out at Mayo Clinic Advanced Genomic Technology Center at Rochester, Minn., USA using the Illumina Genome Analyzer II (GA II) according to the manufacturer's protocol. Data analysis including read alignments, tabulation of detected genes/exons and their levels was completed utilizing the infrastructure and analytic pipelines established at the Mayo Bioinformatics Core.

Nanostring Analysis.

Patient tumor samples were examined by a pathologist and regions that were at least 90% tumor were marked. Indicated regions were scraped and RNA harvested. Isolated RNA was hybridized with the Nanostring probes according to the manufacture's protocol (Nanostring Technologies, Seattle, Wash.). The nCounter Pan Cancer Immune Profiling Panel was employed (Dennis et al., "Multiplexed Cancer Immune Response Analysis: nCounter® PanCancer Immune Profiling Panel for Gene Expression" white paper: NanoString Technologies®, Inc. v1.0 (2014)), custom modified by our laboratory with the addition of 30 gene probes (ADAR, APOBEC3B, APOBEC3C, ddx60, DHX58, PKR, GBP1, GBP3, GBP4, HERC5, HERC6, IFI44, IFI44L, IFI6, IFIT3, IFIT5, IFITM3, IRF9, MX2, OAS1, OAS2, OASL, PVRL4, RSAD2, SAMD9, SAMD9L, Spl00, TRIM21, TRIM22 and TRIM25). Samples were analyzed using the nCounter Digital Analyzer. Nanostring results were analyzed and values normalized to house-keeping genes.

Functional Analysis to Identify a Gene Signature.

RNA-Sequencing gene expression data was obtained from >40 primary GBM patient derived xenograft (PDX) lines. Measles virus (MV) resistant (GBM39, GBM6 and GBM150) and permissive (GBM43 and GBM64) GBM PDX lines were identified as described in the results. Expression data for the resistant and permissive lines were grouped and fold change calculated for each gene. Using the list of genes differentially expressed>1.5 fold and a p-value<0.05, biological functional analysis was performed using GeneCodis software. Genes with changes between sample groups of at least 1.5 fold and p-value at most 0.05 were selected as an input into GeneCodis. GeneCodis outputs a listing of functional groups (GO biological process, GO molecular function, KEGG) with gene/protein IDs assigned to each group. A custom script in R programming language (R Core Team (2016). R: A language and environment for statistical computing. R Foundation for Statistical Computing, Vienna, Austria. URL: https://www.R-project.org/) was used to combine fold change values and p-values with functional grouping of proteins.

DLDA Score Analysis.

RNA-seq data from the PDX lines was processed using Map-RSeq, a Mayo Clinic developed bioinformatics pipeline for RNA sequencing. Sailfish was used to estimate isoform RPKM expression. Nanostring expression data were processed and normalized according to Nanostring's nSolver software.

Both the RNA-Seq and Nanostring expression datasets were reduced to the 790 genes in common between the two datasets (see, e.g., Appendix A). Four genes in the Nanostring data had duplicate probes in the RNA-Seq dataset. The duplicate probe with the longest coding length was selected to be included in the RNA-Seq dataset. To allow analysis on a common scale, the 790 gene expression values for each sample in each dataset were transformed via adding the value of 1.0 to each gene expression value, transforming each value by log 2, and then within each sample standardized to mean=0.0 and standard deviation=1.0. Once standardized using all 790 genes, the 22 ISGs were used for all subsequent analysis.

The dataset for the DLDA model was the 22 ISGs for the 3 resistant (GBM39, 6, 150) and 2 permissive (GBM43 and 64) PDX lines. DLDA predicted value scores (DLDA score) were calculated using this dataset for both the remaining PDX lines and the 10 treated patients. Test-set DLDA scores above 150 and below −250 are classified as resistant and permissive respectively. For the patient DLDA score analysis, a third classification group emerged in relation to virus replication. 6 patients clustered with moderate DLDA scores (−250 to +150) and intermediate levels of virus replication ($1.3 \times 10^3$ to $1.7 \times 10^5$ MV genome copies/μg of RNA). The intermediate patients are permissive to virus replication, however, virus replication was approximately 2-log lower than the other permissive group (<−250).

Quantitative RT-PCR (QRT-PCR).

Total RNA from frozen tumor tissue was extracted using RNeasy kit (Qiagen). On the first step of the reaction cDNA was made using 25 ng of the RNA extracts and One-Step RT-PCR master mix reagents and TaqMan Probe-Based Gene Expression assays (Life Technologies). The assays were run on a Roche 480 Light Cycler instrument (Roche). The relative quantification was performed using human eukaryotic 18S rRNA as a reference. RNA isolated from normal brain or ovarian tissue was used as controls for normal baseline expression in the corresponding organ. Expression was calculated in fold change of expression as compared to corresponding normal tissue control using the comparative CT formula (Pierce).

Quantitative MV N protein RNA expression was analyzed by QRT-PCR in patient frozen tissue samples. Briefly, the quantitative RT-PCR assay was optimized for primers, probe, and magnesium concentration with TaqMan RNA to CT 1-step kit. A 50-μL quantitative RT-PCR reaction volume will be used to amplify the MV-N genomic RNA target, in the presence of 0.3 mmol/L each of forward (5'-GGG TGT GCC GGT TGG A-3'; SEQ ID NO: 1) and reverse (5'-AGA AGC CAG GGA GAG CTA CAG A-3'; SEQ ID NO:2)-primers, 0.2 mmol/L Black Hole Quencher-labeled probe (5'-/56-FAM/TGG GCA GCT CTC GCA TCA CTT GC/3BHQ_1/-3'; SEQ ID NO:3), 4 mmol/L MgCl, and 1 mcg or a maximum total volume of 5 mcl of the RNA isolate. One cycle of reverse transcriptase reaction (15 min at 48° C.) will be applied, followed by a denaturation step (10 min at 95° C.) and 40 cycles of amplification (15 s 95° C. and 1 min 60° C.), with fluorescence measured during the extension. A standard curve of 10-fold dilutions containing $10^7$ to 10 MV-N gene copies/mL will be generated using a manufactured RNA oligo (IDT) Quantification and subsequent calculation of copy number will be done using the standard curve and the ROCHE480 Quantitative PCR System software.

Statistical Analysis.

Statistical analysis was performed using GraphPad Prism 5.0 software (GraphPad Software, San Diego, Calif.) and R version 3.2.3 (R Core Team, 2015 "R: A language and environment for statistical computing. R Foundation for Statistical Computing," Vienna, Austria, available online at R-project.org/).

Results

Differential Response to MV Infection in Primary GBM PDX Lines.

Figure 1A:
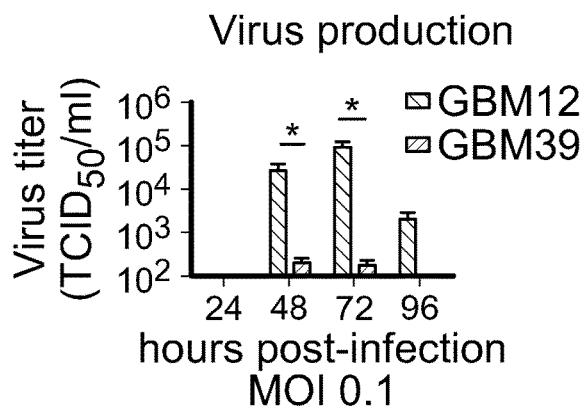
FIG. 1. Constitutive expression of interferon-stimulated genes measured in MV resistant GBM cells. (a) GBM12 and GBM39 cells were infected with MV encoding human sodium iodide symporter (MV-NIS) at multiplicity of infection (MOI) of 0.1 and virus production measured at 24-96 hours (n=3). Infection of GBM12 cells resulted in significant virus production ($6.8 \times 10^4$ tissue culture infectious doses 50% ($TCID_{50}$)/ml); whereas production in GBM39 cells ($1.8 \times 10^2$ $TCID_{50}$/ml) was decreased 387-fold at 72 h (p-value<0.05). (b,c) GBM12 and GBM39 cells were infected with MV-NIS (MOI 1.0 and 0.1) and cell viability assessed by MTT assay (n=3). MV killed>90% of GBM12 cells by day 7, however, approximately 50% of GBM39 cells remained alive by day 7. (d) Athymic nude mice were implanted orthotopically with GBM12 or GBM39 cells (n=10) and received MV therapy ($1 \times 10^5$ $TCID_{50}$/ml) once every 3 days for a total of 3 or 5 doses, respectively. MV therapy in mice implanted with GBM12 cells significantly improved median survival by 37 days. In contrast, MV therapy in mice implanted with GBM39 cells only prolonged median survival by 6 days. (e) GBM12 and GBM39 cells were infected with MV-GFP at a MOI 1.0 and virus entry efficiency measured by GFP positive cells assessed by flow cytometry at 24 hours post-infection (n=2). (f) RNA was extracted from uninfected GBM12 and GBM39 cells and gene expression analyzed by RNA sequencing method (RNA-Seq). A heat-map illustrates the expression of several antiviral interferon-stimulated genes (ISG) over-expressed in GBM39 cells relative to GBM12. (g,h) GBM39 and GBM12 cells were untreated or infected with MV-NIS (MOI 5) and supernatant harvested at 12, 24 and 48 hours post-infection (n=2). IFN-α and IFN-β concentrations were measured by enzyme-linked immunosorbent assay (ELISA) and reached 85.7 and 6,600 pg/ml at 48 hours post-infection, respectively. IFN-α was not detected in GBM12, while IFN-β production peaked at 24 hours post-infection (92.6 pg/ml). IFN-β was not detected in uninfected GBM39 cells, despite constitutive ISG expression (detection limit>50 pg/ml). ND, not detectable; ns, not significant; statistical analysis two-tailed student t-test; *p<0.05; **p<0.01. Data are presented as the mean+/−s.e.m.
Figure 1B:
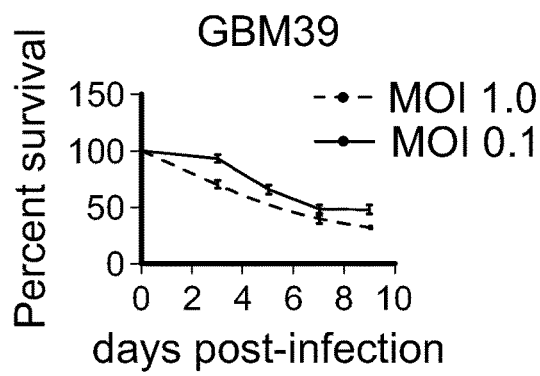
Figure 1C:
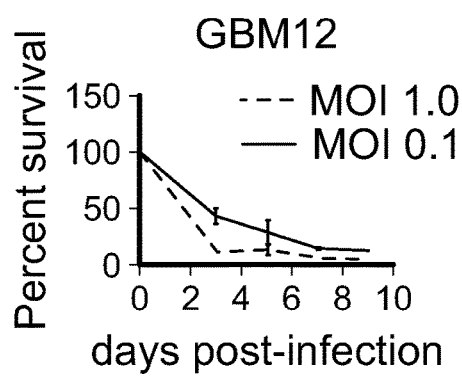
Figure 1E:
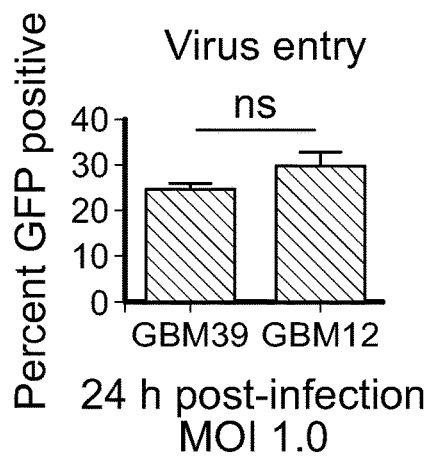
Figure 1D:
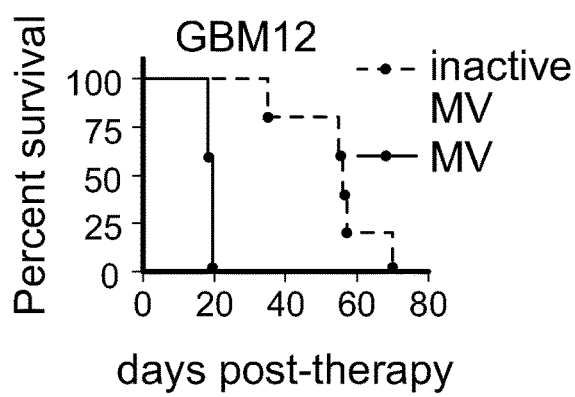
Figure 1D:
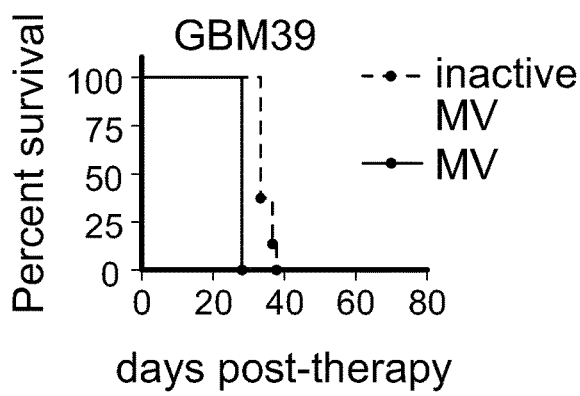
Figure 1F:
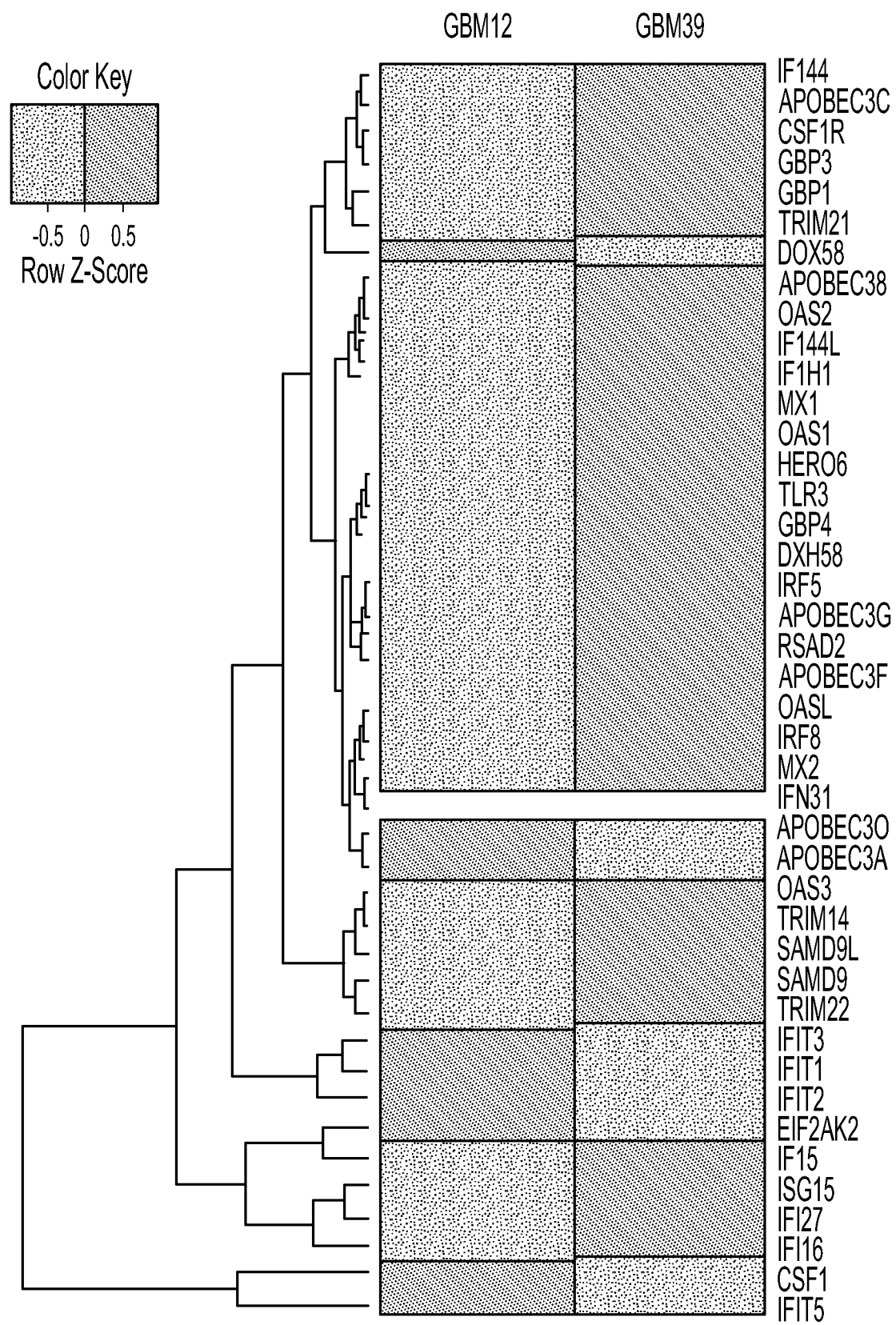

To characterize differential responses to oncolytic MV for the treatment of GBM, MV replication in a MV resistant (GBM39) and MV permissive (GBM12) primary patient-derived GBM xenograft (PDX) lines was evaluated. These lines are derived from resected human GBM patient tumors propagated as xenografts, and following orthotopic implantation have been shown to maintain the molecular characteristics and invasiveness of their human tumor of origin. Upon infection with the MV strain MV-NIS (which is currently in clinical testing) at a MOI of 0.1 for 24-96 hours, virus production in GBM12 cells reached $6.8 \times 10^4$ tissue-culture infection dose 50% per ml ($TCID_{50}$/ml) at 72 hours with complete destruction of the cell monolayer (FIG. 1a, c). In comparison, virus production in GBM39 cells reached $1.8 \times 10^2$ $TCID_{50}$/ml (387-fold lower infectious progeny; p-value<0.05) and more than 40% of GBM39 cells remained alive 7 days post-infection (FIG. 1a,b). We next sought to confirm the observed in vitro differences in response to MV therapy in an orthotopic in vivo model. Mice implanted with GBM12 cells responded to MV therapy with a 37 day prolongation in median survival. In comparison, the MV treated GBM39 animal group demonstrated only a 6 day prolongation in survival (FIG. 1d).

To identify a mechanism for the observed differences in response to oncolytic MV, MV entry into the GBM cells using a MV encoding a green fluorescent protein (GFP) reporter was first evaluated. MV enters GBM12 and GBM39 cells at a similar efficiency (29% and 24%, respectively; p-value n.s.), as measured by flow cytometry (FIG. 1e). Additionally, both GBM12 and GBM39 cells have similar levels of CD46, SLAM and Nectin-4 entry receptor expression, suggesting a mechanism of post-entry restriction (FIG. 2). Therefore, RNA-Seq analysis was performed on uninfected GBM12 and GBM39 cells. While multiple genes were differentially expressed between the 2 lines, a key difference relevant to virotherapy was the constitutive expression of interferon-stimulated genes (ISG), such as MX1, MX2, IFI35, OAS2, and IFI44 (Figure if). Importantly, constitutive expression of the ISGs was independent of IFN-β production (FIG. 1g).

Infection with MV (MOI 5) induces production of IFN-β in GBM39 cells (6,600 pg/ml) 24 hours post-infection; whereas production is delayed and significantly lower in GBM12 cells upon infection (92.6 pg/ml) (FIG. 1g). Additionally, infection led to production of IFN-α by 48 hours (85.7 pg/ml) in GBM39 cells, whereas IFN-α was not detectable in infected GBM12 cells up to 48 hours post-infection (FIG. 1h). These results indicate that resistance to the virus is not due to differences in receptor expression, but rather, GBM39 cells are in an ISG mediated pre-existing antiviral state. The pre-existing antiviral state primes cells to mount a rapid and robust antiviral response upon infection, which possibly confers resistance to oncolytic MV infection (Phipps-Yonas et al., 2008 PLoSPathog 4:e1000193).

Constitutive Activation of the Type I Interferon Pathway in MV Resistant GBM Cells.

Figure 3A:
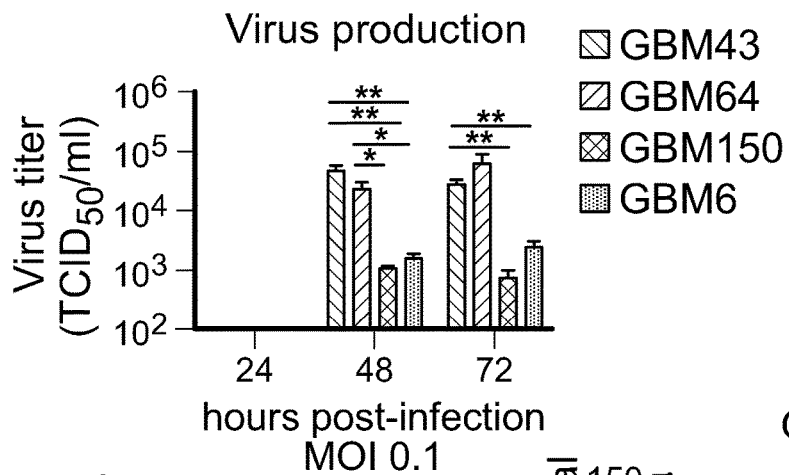
FIG. 3. Gene-set enrichment analysis (GSEA) identifies important interferon stimulated genes differentially expressed between MV resistant and permissive GBM lines. (a) Additional primary GBM lines were infected with MV at a MOI 0.1 and virus production measured by titration on Vero cells 24-72 hours post-infection. Virus production in GBM43 and GBM64 cells (>$2.0 \times 10^4$ $TCID_{50}$/ml) was significantly greater than production in GBM6 and GBM150 (<$1.6 \times 10^3$ $TCID_{50}$/ml) (n=3) (p-value<0.05). (b-e) Cell killing measured by MTT assay demonstrated that GBM64 and GBM43 cells were effectively killed upon infection with MV-NIS (MOI 1.0 and 0.1) with elimination of monolayer cultures at 96-144 hours post infections; whereas more than 40% of GBM6 and GBM150 cells remained alive in the same time-frame (n=3). (f) Gene expression for GBM64, GBM43, GBM150 and GBM6 cells was measured by RNA-Seq. Cells were grouped according to their response to MV. The resistant group consists of GBM39, GBM6, and GBM150, while the permissive group consists of GBM43 and GBM64. GSEA was performed on the MV resistant and permissive groups to identify pathways differentially activated between the two groups. The top 15 pathways over-represented in the resistant group are listed and indicate the type I interferon pathway as the second most differentially expressed pathway (p-value 2.14E-20). ND, not detectable.
Figure 3B:
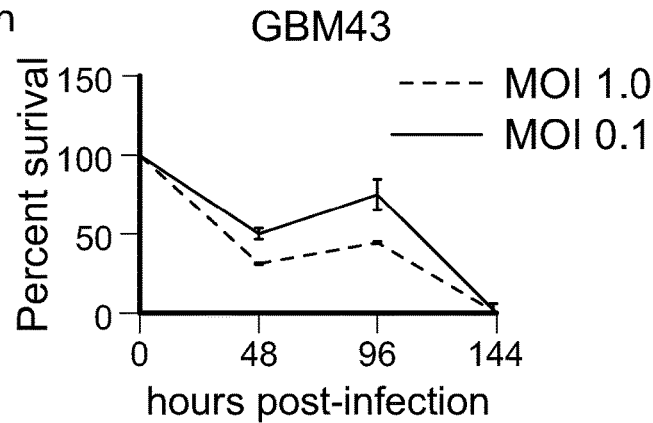
Figure 3C:
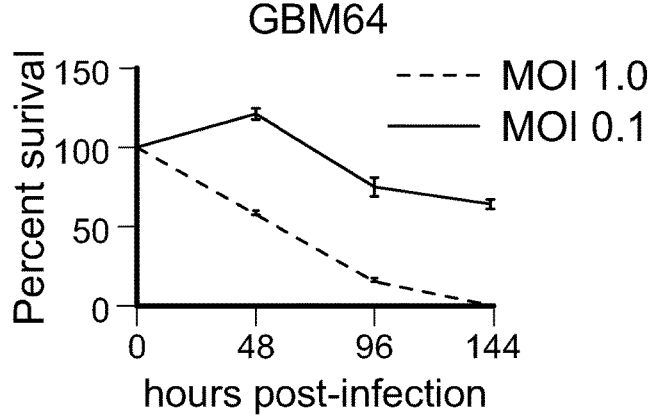
Figure 3D:
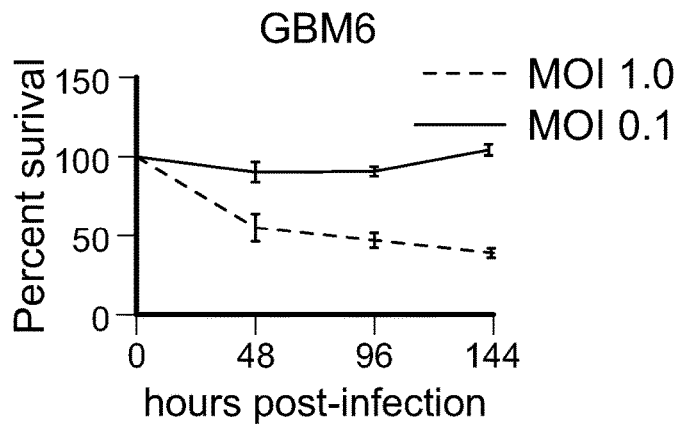

To determine the prevalence and effect that constitutive expression of ISGs may have on oncolytic MV therapy, 4 additional permissive and resistant GBM lines deriving from human patients were identified. Virus production was measured in primary GBM cells 24-72 hours after infection with MV-NIS (MOI=0.1). GBM43 and GBM64 cells supported MV replication (>2.0×10$^4$ TCID$_{50}$/ml), whereas replication in GBM6 and GBM150 cells was significantly lower (<1.6× 10$^3$ TCID$_{50}$/ml) (p-value<0.05) (FIG. 3a). In line with these differences in MV replication, 100% of GBM43 and GBM64 cells were effectively killed upon MV infection, whereas approximately 30% of GBM6, and GBM150 cells survived 7 days post-infection (FIG. 3b-e).

In a parallel study, gene expression was examined by RNA-Seq analysis using RNA isolated from tumors of mice orthotopically implanted with 41 different primary GBM PDX lines, including GBM6, 150, 39, 43, 12 and 64. Expression data for GBM12 was excluded due to poor RNA quality. Using this expression data, gene set enrichment analysis (GSEA) was performed to identify differential pathway activation between the resistant (GBM39, 6, and 150) and permissive lines (GBM43 and 64). The "Protein binding pathway" is the most differentially expressed pathway (p-value 6.12×10$^{31}$), while constitutive activation of the type 1 interferon pathway in the resistant group is the second most differentially activated pathway (p-value 2.14×10$^{-20}$) (FIG. 3f). The type 1 interferon pathway was focused on the due to the known antiviral functions of this pathway. 22 genes involved in the interferon pathway are differentially expressed (>1.5 fold and p-value<0.05) between the resistant and permissive group. Importantly, induction of ISGs with exogenous IFN-β in permissive cells prior to infection leads to MV resistance (FIG. 4).

IFN Activation as a Predictive Marker for Response to Oncolytic MV Therapy.

Figure 5A:
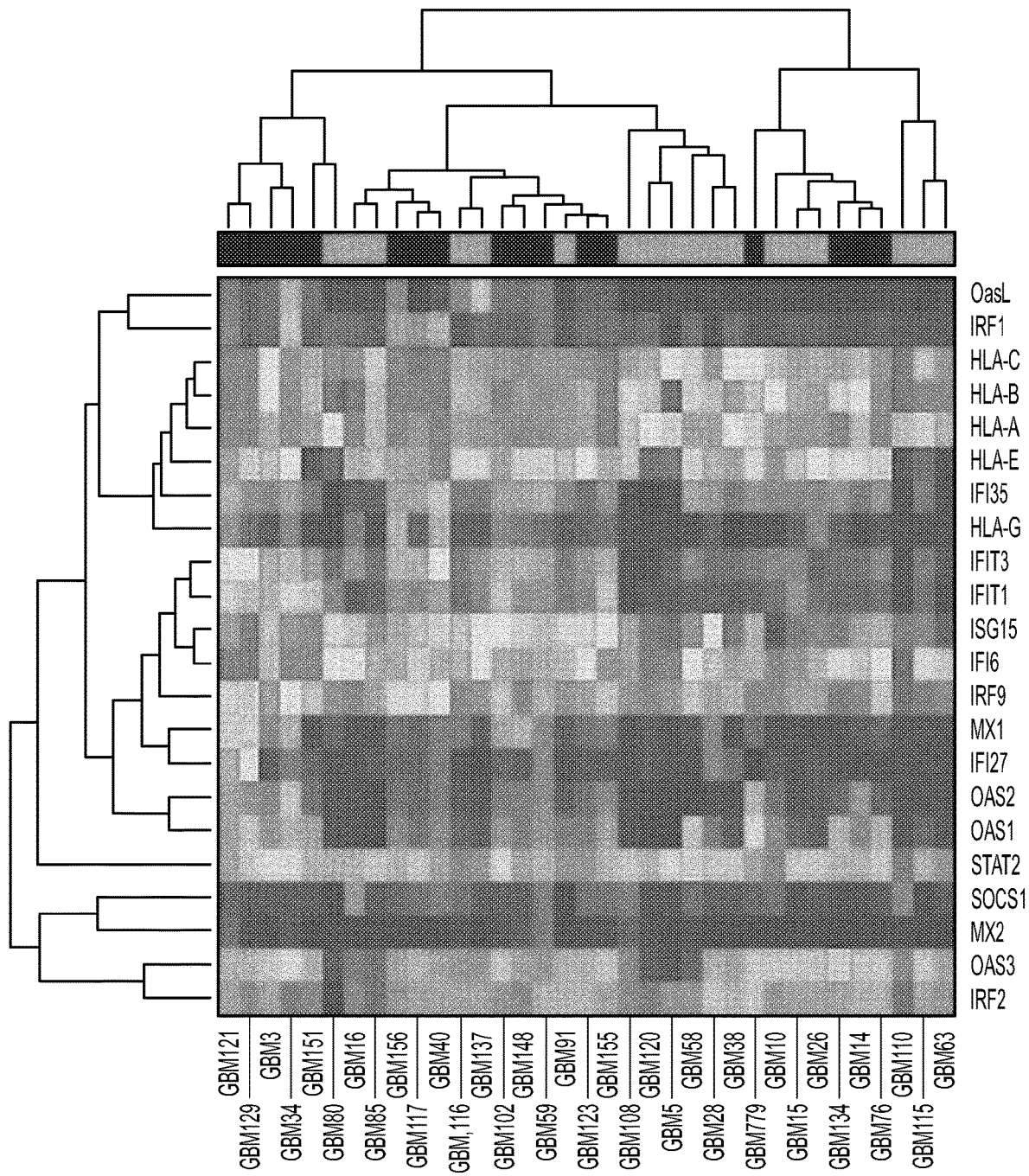
Figure 5G:
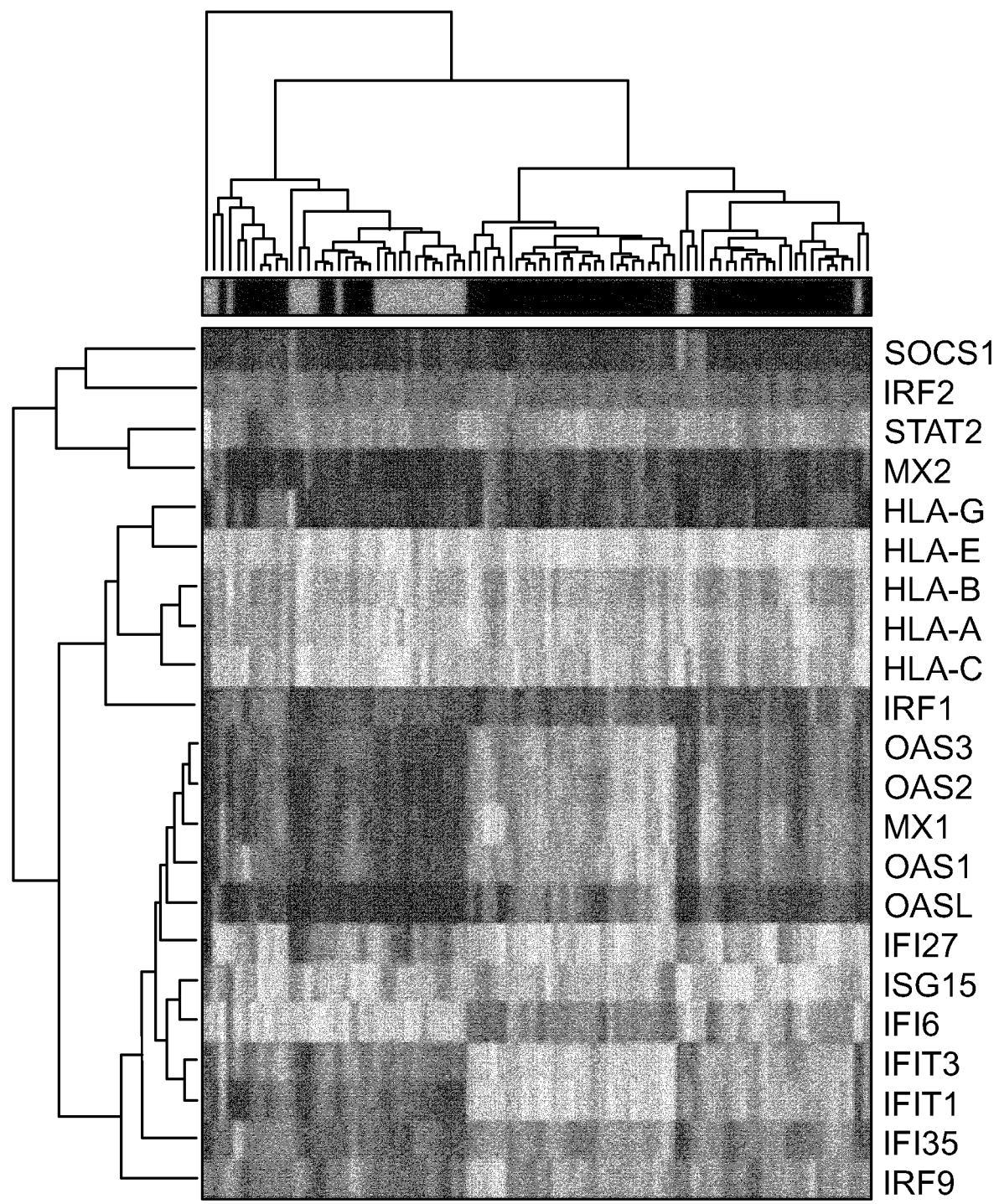
Figure 5I:
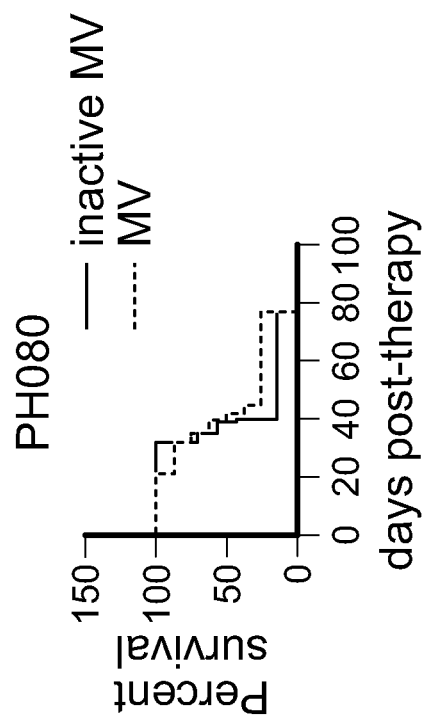

To determine if activation of the interferon signaling pathway could serve as an indicator to predict outcome upon oncolytic MV therapy, 22 genes identified in the pathway analysis were used as a gene signature to predict response to MV therapy in primary GBM PDX lines. First, gene expression was examined in the remaining 35 GBM PDX lines and performed unsupervised hierarchical clustering using the 22 ISGs (FIG. 5a). To predict response to MV in GBM PDX lines, the Diagonal Linear Discriminant Analysis (DLDA) class prediction algorithm was utilized. The training dataset for the DLDA model consists of expression for the 22 ISGs in the 3 resistant (GBM39, 6, 150) and 2 permissive (GBM43, 64) PDX lines. The DLDA scoring algorithm uses the training models to determine the significance of each gene and assigns a unique coefficient number to each gene. DLDA scores for test samples are calculated using this specific gene list and corresponding coefficient for each gene. Test-set DLDA scores above and below 0.0 are classified as resistant and permissive, respectively. PDX lines classified as resistant or permissive are indicated by a gray or black bar, respectively (FIG. 5a).

Of the 35 primary GBM PDX lines tested, 18 were predicted to be responders. To test the use of constitutive interferon activation as a method to predict outcome, PDX lines classified as responders or non-responders were challenged with MV. MV production was measured at 24-96 hours post-infection. MV production in the line assigned to the responders (GBM10) reached high levels of virus production (1.4×10$^5$ TCID$_{50}$/ml), whereas MV production in the PDX lines designated as a non-responder (GBM76) only reached 2.2×10$^3$ TCID$_{50}$/ml at 72 hours (FIG. 5b). In line with the decreased virus production, cell killing was significantly impaired in the resistant line relative to the predicted responder (FIG. 5c,d). In vitro results were confirmed in mice orthotopically implanted with tumor cells. Intratumoral injection with 3 doses of MV-NIS (1×10$^5$ TCID$_{50}$/dose) in mice implanted with MV permissive GBM10 cells significantly improved median survival (p-value<0.0001). In contrast, mice implanted with MV resistant GBM76 cells demonstrated no significant difference in median survival when treated with 5 doses of MV-NIS (85 vs 89 days, p-value 0.1324) (FIG. 5e,f).

Figure 5H:
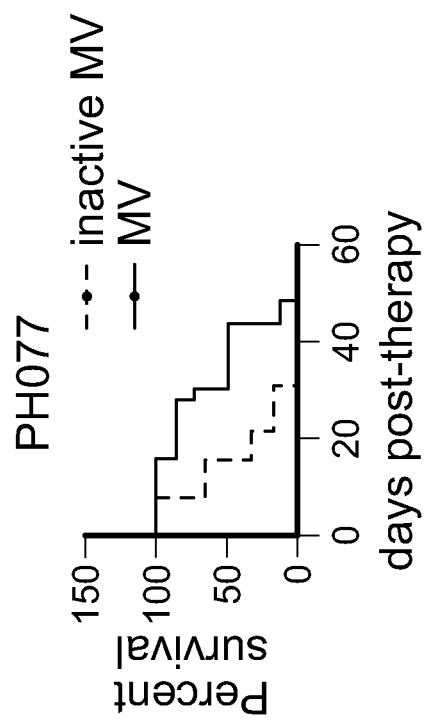

To validate the predictive ISG based algorithm in other tumor types, we examined gene expression in 86 OvCa PDXs and each line predicted as a "responder" or "non-responder" using the DLDA prediction algorithm described above (FIG. 5g). Approximately 27% (23 of 86) primary lines were predicted to be permissive. A predicted responder (PH077) and non-responder (PH080) were randomly selected and challenged with MV therapy. MV therapy in mice implanted with PH077 resulted in a significant 22-day prolongation in median survival upon MV-NIS therapy (3 doses of 1×10$^5$ TCID$_{50}$ once/week) (p-value=0.0098). In comparison, mice implanted with PH080 received no benefit with MV therapy (p-value=n.s.) (FIG. 5h,i).

Constitutive ISG Expression Inversely Correlates with Infection in MV Treated GBM Patients.

Figures 6A, 6B:
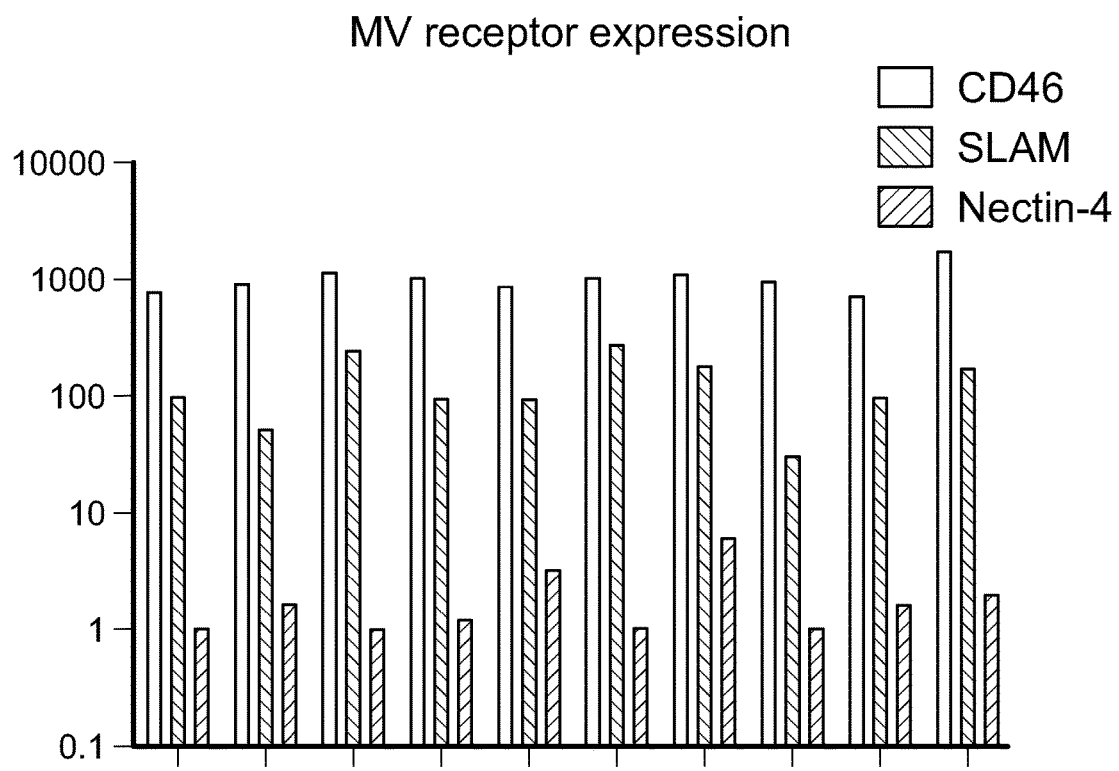

To further validate the baseline ISG expression level as an indicator for response to MV therapy, tumors of GBM patients treated with MV in an ongoing phase I clinical trial were examined. Patient response to therapy was assessed by virus replication measured in the resected tumor (qRT-PCR for MV genome copies/μg of RNA). Virus replication in treated patients was analyzed 5 days post-therapy and ranged from non-detectable to 6.0×10$^7$ genome copies/μg RNA (FIG. 6a).

Figure 6C:
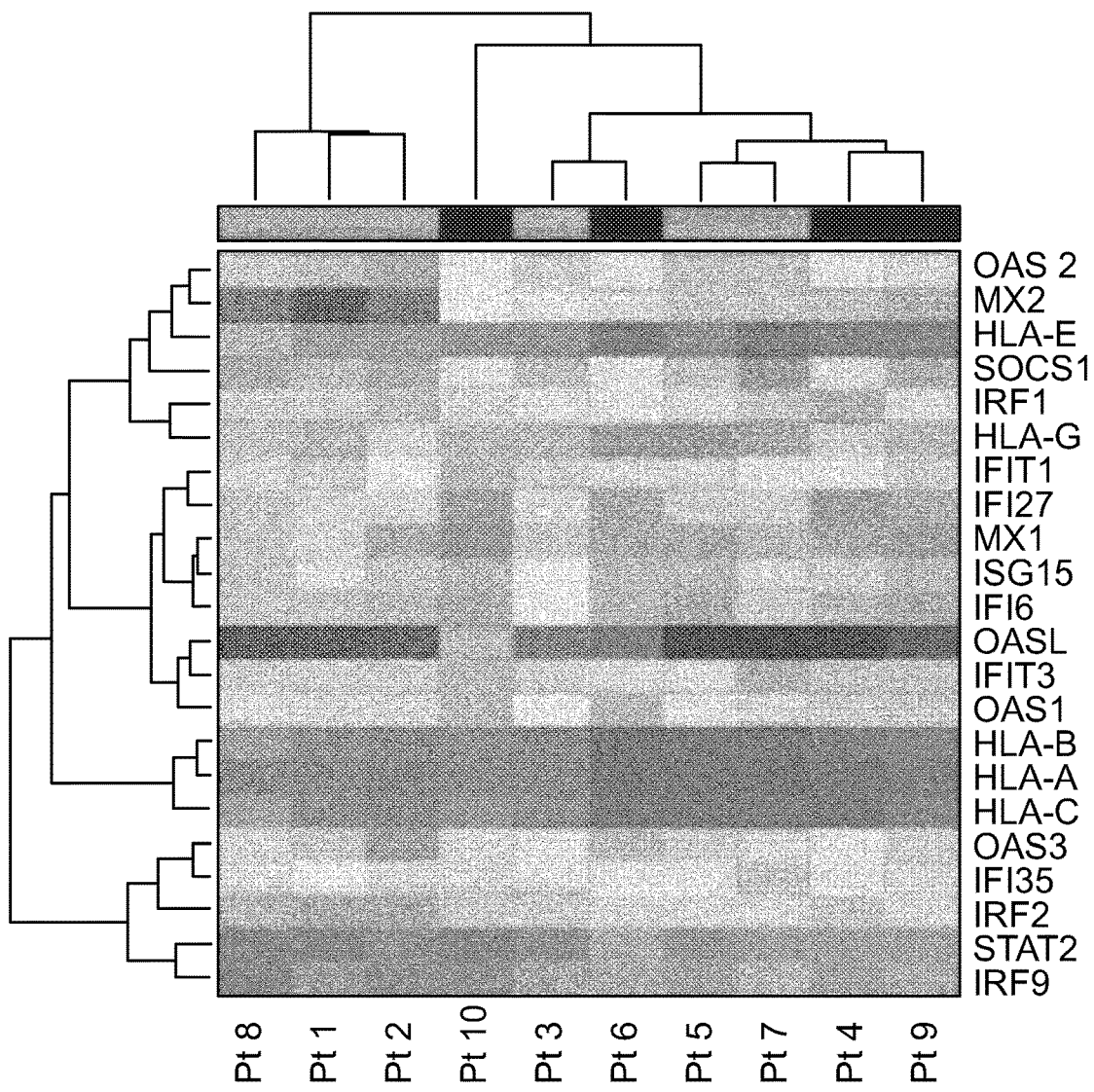
Figure 6D:
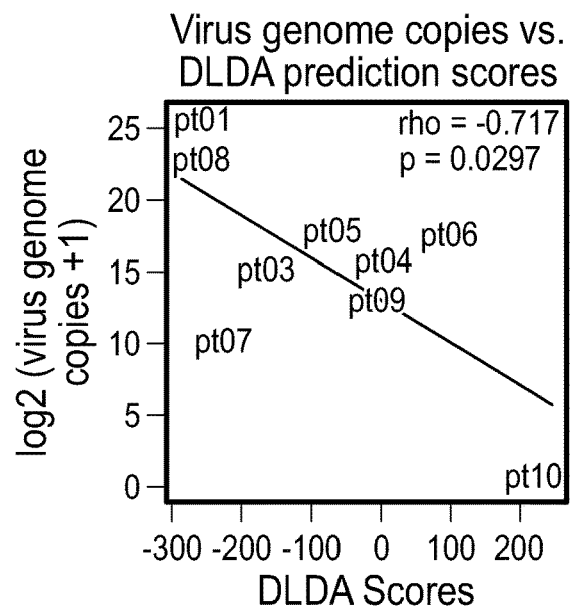

Nanostring technology was utilized to assess gene expression using a custom 800 gene panel. Expression of the MV entry receptors was similar among the 10 treated patients, suggesting a mechanism of post-entry restriction (FIG. 6b). In order to determine if the algorithm we developed in xenografts could be predictive of oncolytic virus replication in treated patients, the DLDA scoring system was utilized in 10 consecutive GBM patients who received MV as part of a dose escalation trial (NCT00390299); 2 patients had received 2×10$^6$ TCID50 and 8 patients 2×10$^7$ TCID50. Patients had their tumors resected on day 5 post initial viral administration. As described above, test-set DLDA scores for each patient were generated using the training set PDX data with the 22 gene interferon signature (FIG. 6c). An increase in the DLDA score (elevated ISG expression) was inversely correlated with the virus replication measured in the patient's tumor (p=−0.717; p-value=0.0297) (FIG. 6d). Importantly, the patient with the highest DLDA score (above 150) had no detectable virus, whereas the 2 patients with the lowest DLDA scores (below −250) had the highest level of viruses ($6.8 \times 10^6$ and $6.0 \times 10^7$ MV genome copies/µg of RNA) recovered from the tumor. Interestingly, patient-1 had the lowest DLDA score and highest level of virus replication detected, despite receiving the lowest viral doses ($2 \times 10^6$ TCID$_{50}$) (FIG. 6a,d). The remaining six patients had moderate DLDA scores (−250 to +150) and intermediate levels of virus replication ($1.3 \times 10^3$ to $1.7 \times 10^5$ MV genome copies/µg of RNA). These intermediate patients were permissive to virus replication; however, virus replication was approximately 2-log lower than the group with higher permissiveness. Overall, these results are consistent with our hypothesis that ISG expression can determine MV permissiveness and serve as a screening tool with recommended thresholds or below −250 (permissive), −250 to 150 (intermediate), and above 150 as resistant.

JAK1 Inhibition Overcomes Resistance to MV Infection.

Figure 7A:
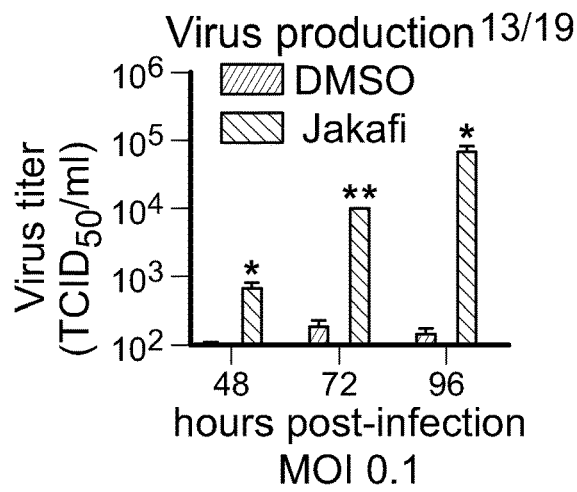
Figure 7B:
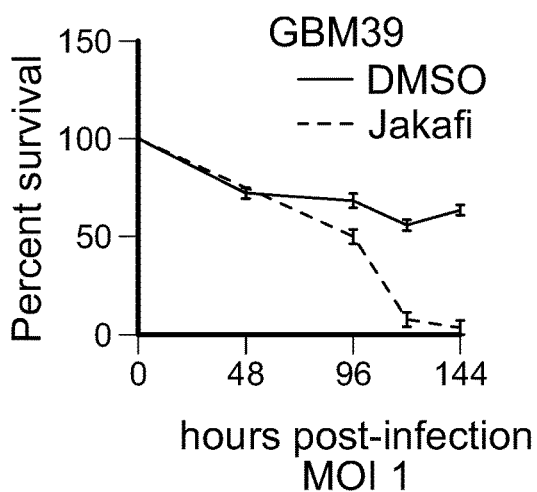
Figure 7C:
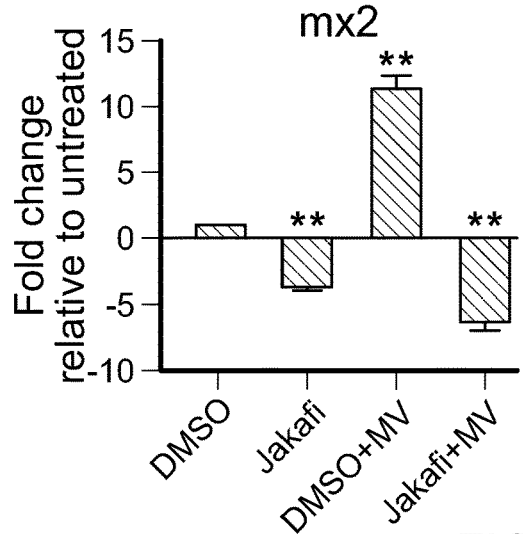
Figure 7D:
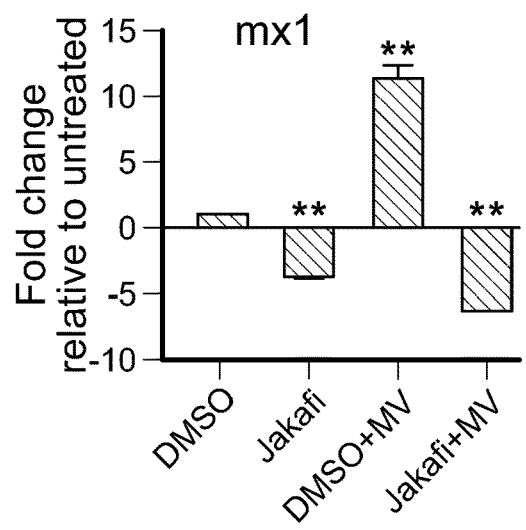
Figure 7E:
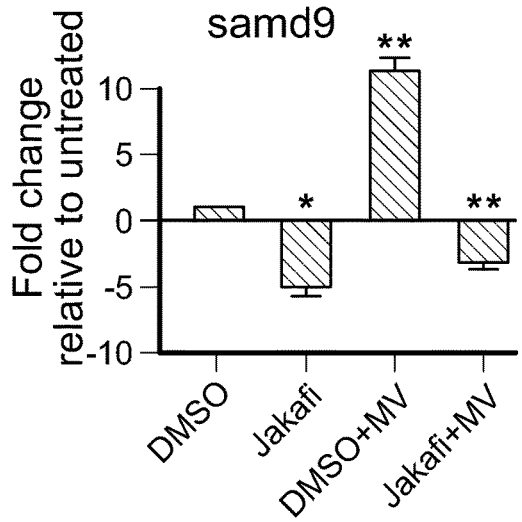
Figure 7F:
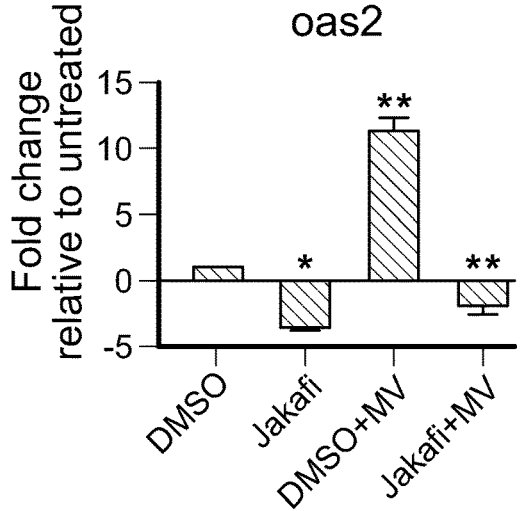
Figure 7G:
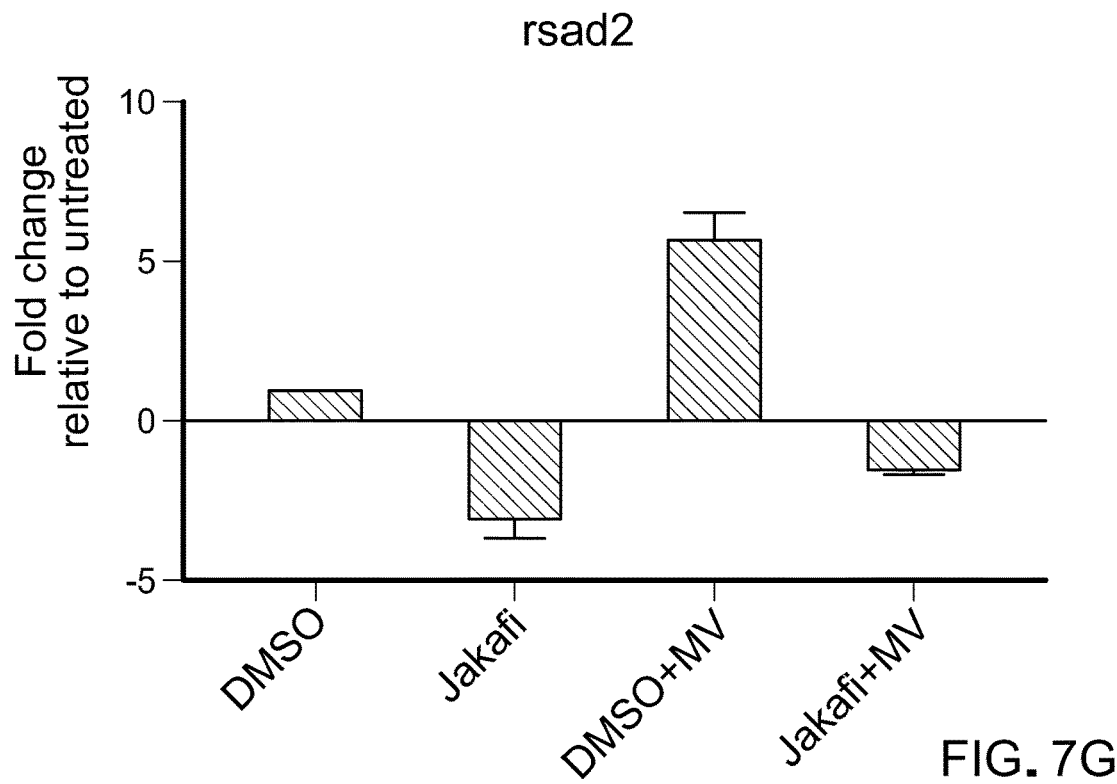
Figure 8A:
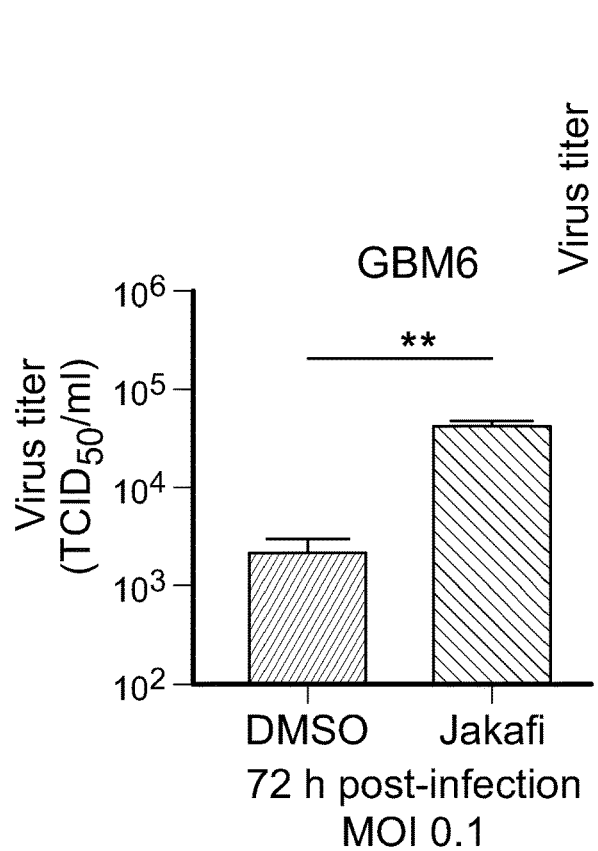
Figure 8A:
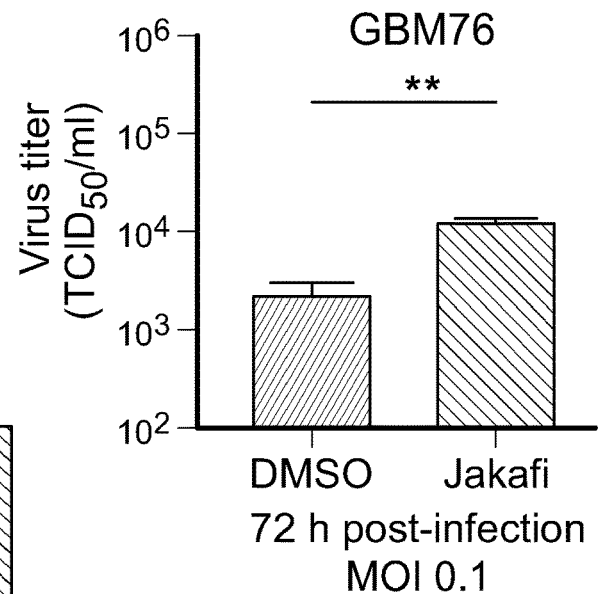
Figure 8B:
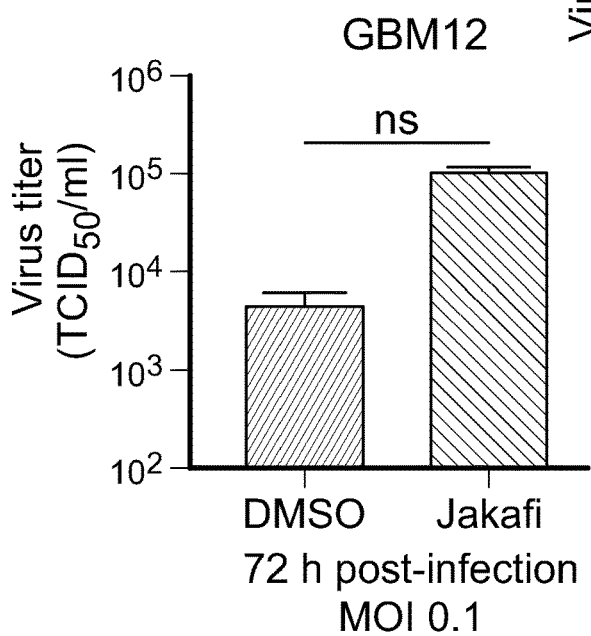
Figure 8B:
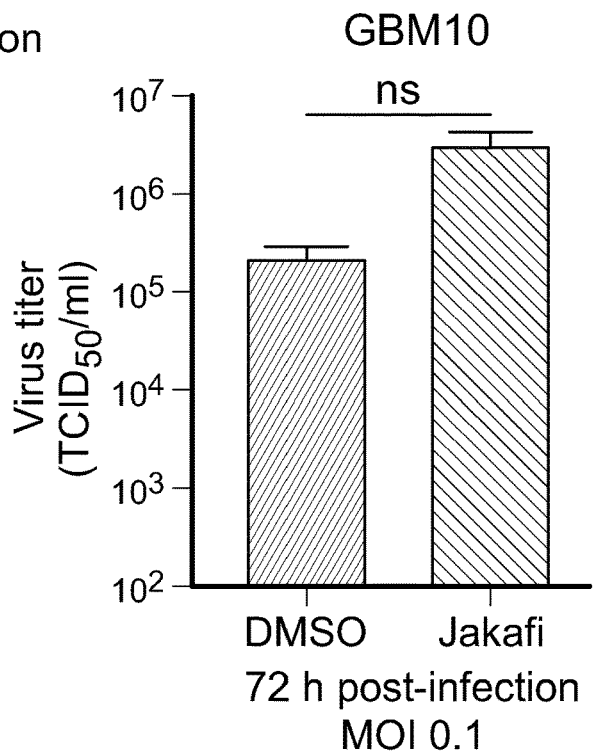

Upon viral infection, the host antiviral defense mechanism triggers IFN production and signaling through the JAK/STAT pathway to activate more than 300 ISGs (Silvennoinen et al., 1993 Nature 366:583-585). Therefore, the use of pharmacological agents to overcome resistance through chemical inhibition of the JAK/STAT pathway was explored. GBM39 cells were treated with 3 µM Jakafi for 48 hours prior to infection with MV-NIS (MOI 0.1). Virus production was significantly increased at 48 hours post-infection and nearly 1000-fold greater by 96 hours (FIG. 7a). The increased virus production and spread also led to increased cell killing in Jakafi pre-treated cells relative to control treated cells (FIG. 7b). A similar result was measured in 4 additional resistant and permissive lines (FIG. 8a,b).

To determine the mechanism for overcoming resistance, cells were treated with 3 µM of Jakafi or DMSO control for 48 hours. RNA was harvested and ISG expression analyzed by qRT-PCR. Relative to control treated cells, expression of RSAD2, OAS2, MX1, MX2 and SAMD9 were significantly decreased, suggesting that persistent baseline JAK1 activation contributes to constitutive ISG expression (FIG. 7c-g). Furthermore, pretreatment with Jakafi blocked ISG induction upon MV infection (MOI 5), whereas ISG expression was significantly increased upon infection in the control treated cells.

Figure 7H:
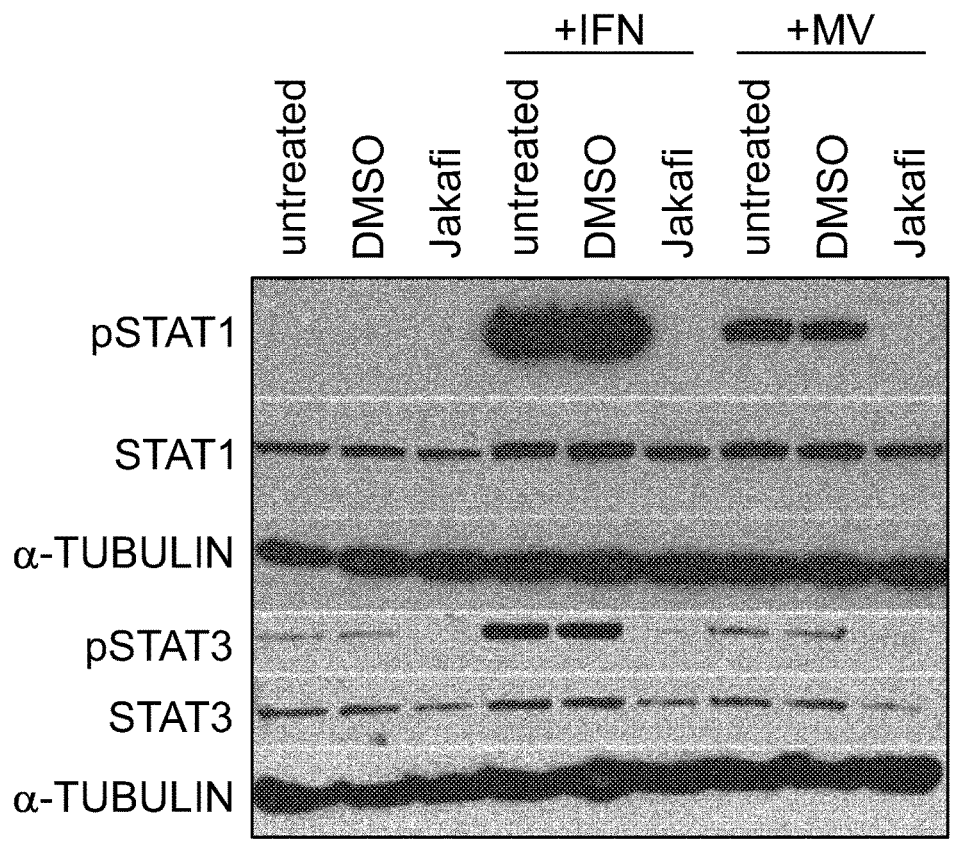
Figure 7I:
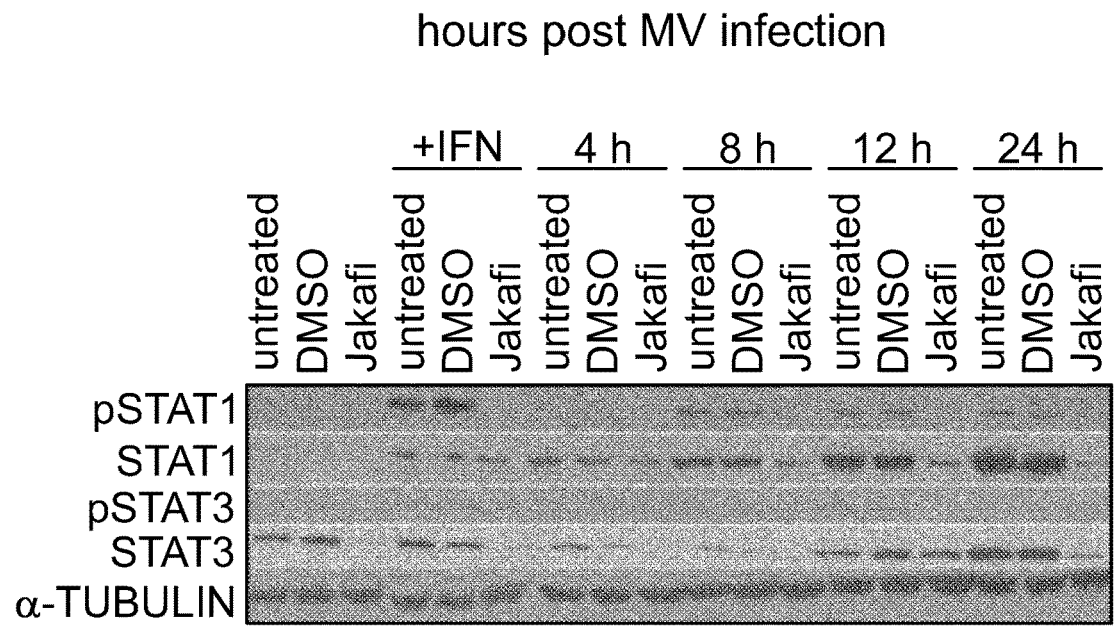
Figure 7J:
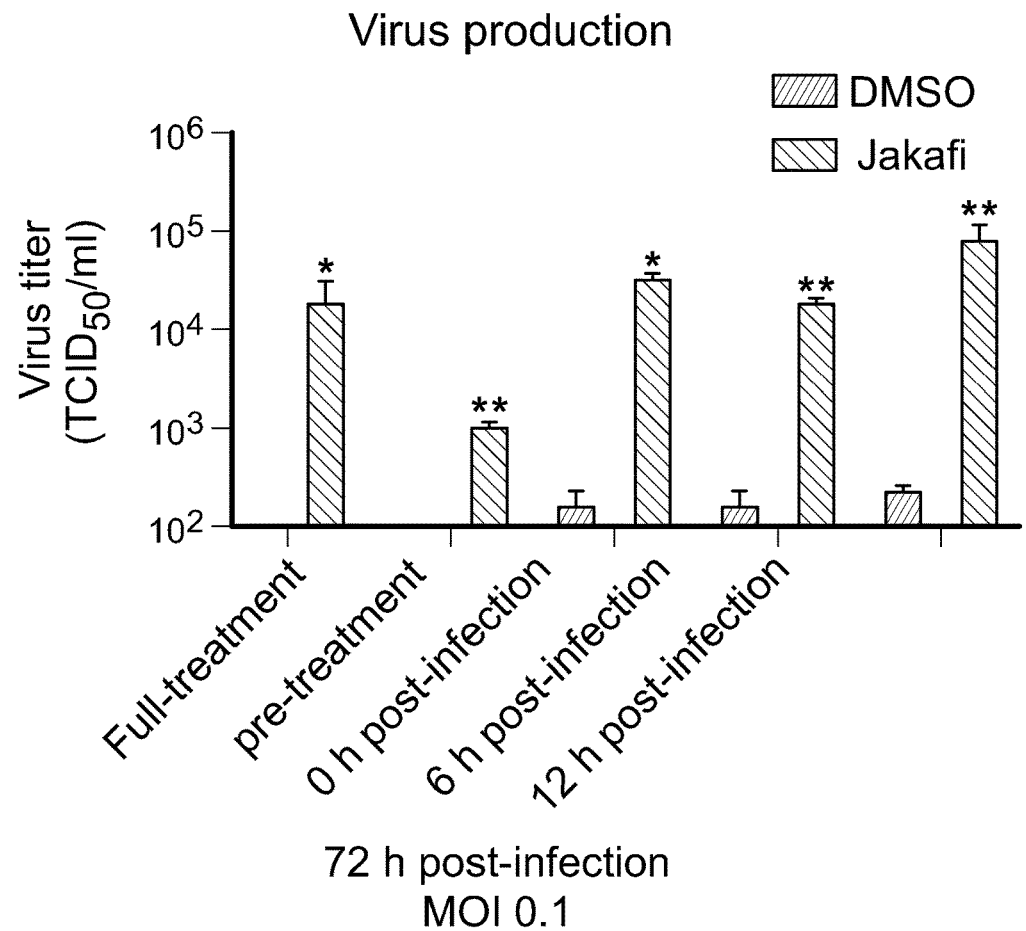
Figure 9A:
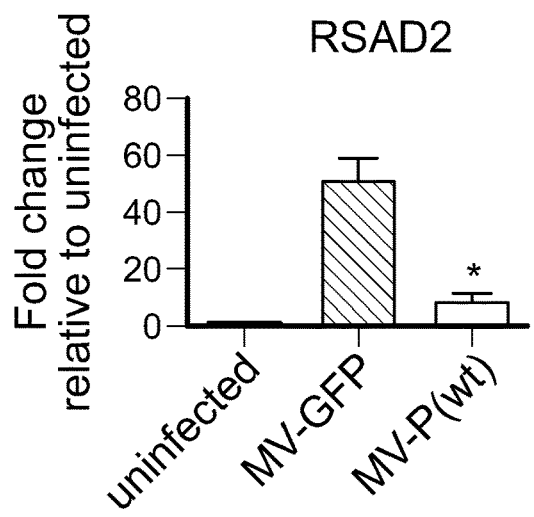
Figure 9A:
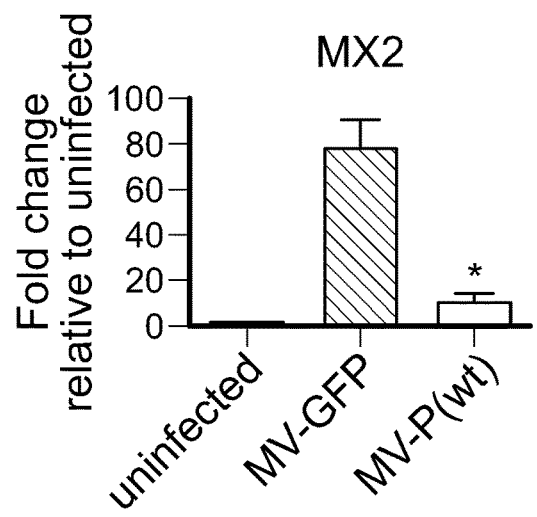
Figure 9A:
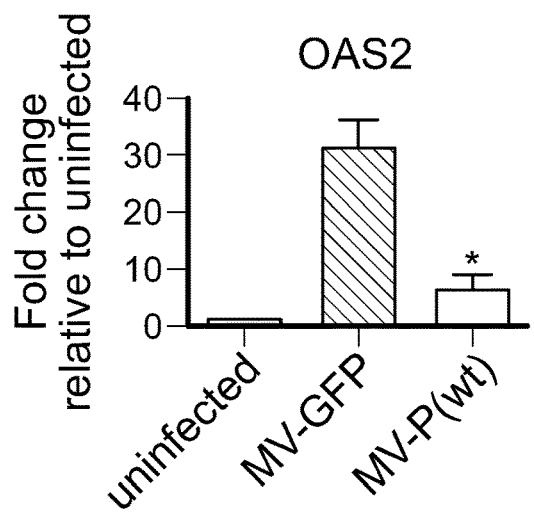
Figure 9A:
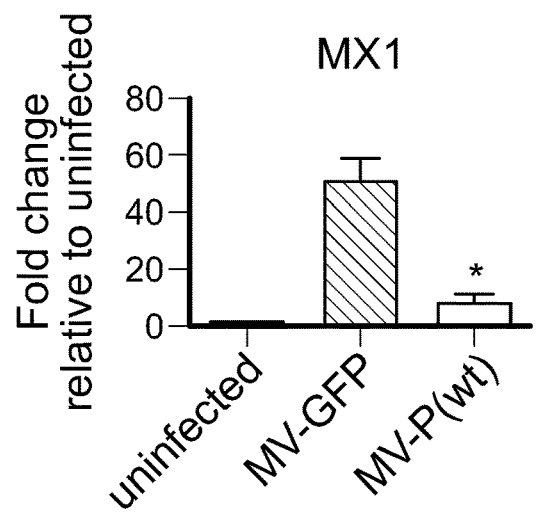
Figure 9A:
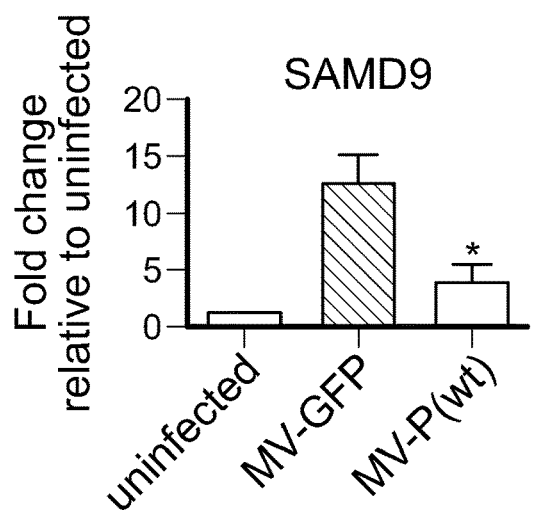
Figure 9B:
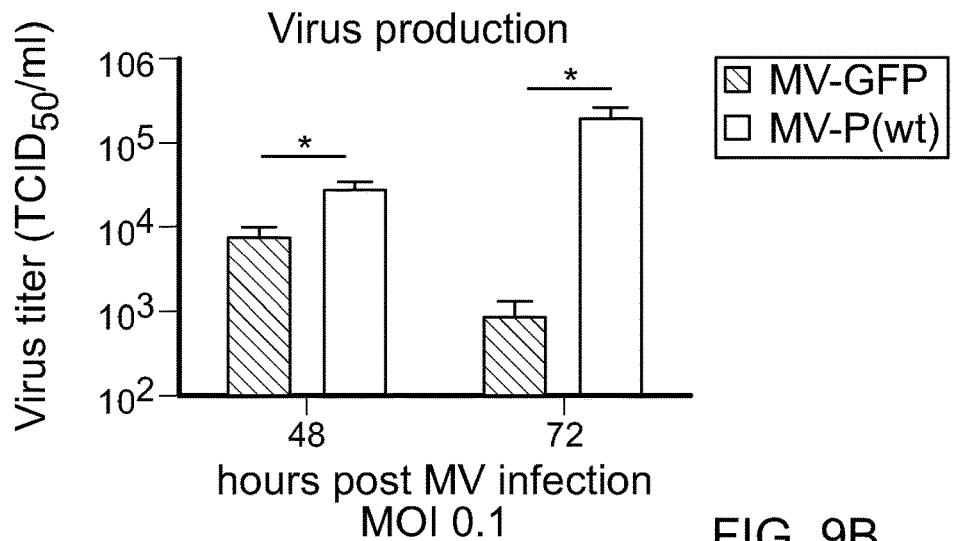

The signaling molecules involved in mediating the constitutive expression and induced expression of ISG following MV infection were next investigated. Activation of STAT1 and STAT3 was analyzed by phosphorylation at Tyr701 or Tyr705, respectively, by western blot in uninfected and MV-infected GBM39 cells (MOI 5, 4 hours post-infection). Interestingly, STAT3 is constitutively activated in the uninfected cells, whereas activated STAT1 was not detected. Phosphorylation of both STAT1 and STAT3 was induced upon infection; however this process was inhibited in the presence of Jakafi (FIG. 7h). A similar, but delayed response was observed in GBM12 cells (FIG. 7i). Furthermore, we treated GBM39 cells with Jakafi at different times during the course of MV infection to determine when restriction could be overcome. Cells were treated with 3 M Jakafi for either 48 hours prior to infection and maintained in the drug during the course of infection, 48 hours pre-treatment only, at the time of infection, 6 hours post-infection, or 12 hours post-infection. Jakafi added up to 12 hours post-infection is sufficient to restore MV production to levels similar with a full course of Jakafi treatment (FIG. 7j). These results suggest that inhibition of the antiviral response is critical for propagating infection in resistant lines, confirming the priming effect described above. Additionally, we challenged resistant cells with a recombinant MV encoding the wild-type phosphoprotein (MV-P(wt)). The phosphoprotein gene of wild-type MV encodes the P/V/C proteins and has been show to play an important role in inhibiting IFN induction and signaling (Devaux et al., 2013 Virology 444:250-256; Devaux et al., 2004 J Virol 78:11632-11640; Nakatsu et al. 2008 J Virol 82:8296-8306). Infection with MV-P(wt) leads to a significant decrease in ISG induction relative to infection with MV-GFP and can successfully replicate in resistant GBM39 cells (FIG. 9a,b). Overall, these results highlight the importance of utilizing the basal ISG expression profile as a reliable indicator for responsiveness to MV therapy and suggest that pharmacologic inhibition and modification (including genetic manipulation of the vector backbone or insertion of therapeutic transgenes) of the viral strains are promising strategies to circumvent primary resistance.

These results demonstrate that decreased levels of expression of ISGs set forth in Table 1 by cancer cells can be used to determine, prior to treatment, whether or not the cancer cells in a given cancer patient are likely be responsive to virotherapy.

Example 2: Analysis of Ovarian Cancer Cells Responsive to Oncolytic Virus Treatment Methods Patients and Patient Samples.

All studies involving patients were approved by the Mayo Clinic Institutional Review Board. Written informed consent was obtained for all patients. As part of 2 separate phase I clinical trials, patients with recurrent ovarian cancer (OvCa) were treated with increasing doses of MV-CEA (NCT00408590) (Galanis et al. 2010, Cancer Research 70(3): 875-882). Upon recurrence, patients received several intraperitoneal injections of MV over the course of several months.

RNA was isolated from 8 frozen tumor tissue samples collected from OvCa patients at the time of primary surgery. To avoid normal tissue, tumor cells were identified by a pathologist and scraped from the histology slides. RNA was subsequently isolated and TruSeq with polyA selection was used to generate libraries. The RNA-Seq data was analyzed using MAP-RSeq v.1.2.1.3, the Mayo Bioinformatics Core pipeline (Kalari et al. 2014, BMC Bioinformatics 15:224). MAP-RSeq consists of alignment with TopHat 2.0.6 against the hg19 genome build and gene counts with the HTSeq software 0.5.3p9 (huber.embl.de/users/anders/HTSeq/doc/overview.html) using gene annotation files obtained from Illumina (support.illumina.com/sequencing/sequencing_software/igenome.html) (Kim et al. 2013, Genome Biology 14(4): R36).

Results

Elevated ISG Expression in the Tumors of MV Treated OvCa Patients.

To validate the predictive ISG based algorithm in other tumor types, gene expression in patients with recurrent ovarian cancer (OvCa) treated with MV-CEA was examined. OvCa patients were injected with increasing doses of MV-CEA ($10^3$-$10^6$ TCID$_{50}$) intraperitoneally upon tumor recurrence. Gene expression of the ISG gene signature was measured using RNA-Seq in the primary tumors of 7 patients. DLDA scores were calculated for each patient using the training set described in the GBM patients. 3 of the 7 patients were predicted to be responders (FIG. 10). Unlike the GBM patients, post-MV therapy tissue was not available to assess virus replication efficiency. Given similar eligibility criteria, progression free survival upon viral treatment was used as a surrogate of benefit. Patient OV-1551 was removed from the trial due to abdominal infection, unrelated to therapy and as such, was not evaluable for response. OV-1002 and OV-1029 were both predicted to be responders. Interestingly, both patients benefited significantly from MV therapy and had the best response among the 7 patients, in terms of time to progression. Time to progression in the remaining 4 patients predicted to be non-responders was not prolonged with disease progression being experienced within 1-2 months from treatment initiation.

These results demonstrate that the ISG signature and DLDA score can be used to determine, prior to treatment, whether or not a patient with ovarian cancer is likely be responsive to virotherapy.

Example 3: ISG-DLDA Coefficients and Model Constants

Training datasets for the Diagonal Linear Discriminant Analysis (DLDA) model have 22, 12, or 6 ISGs for the 3 resistant (GBM39, 6, 150) and 2 permissive (GBM43, 64) PDX lines. Using these training datasets coefficients and constants have been calculated for use with subsequent samples.

TABLE 4

ISG-DLDA Coefficients

| ISG Gene Symbol | 22 ISGs | 12 ISGs | 6 ISGs |
| --- | --- | --- | --- |
| HLA-A | 34.35067 | 34.35067 | 0 |
| HLA-B | 16.63304 | 0 | 0 |
| HLA-C | 80.03653 | 80.03653 | 80.03653 |
| HLA-E | 7.939461 | 0 | 0 |
| HLA-G | 20.69257 | 20.69257 | 0 |
| IFI27 | 2.801251 | 0 | 0 |
| IFI35 | 7.915572 | 0 | 0 |
| IFI6 | 47.07211 | 47.07211 | 47.07211 |
| IFIT1 | 42.98597 | 42.98597 | 42.98597 |
| IFIT3 | 18.71784 | 18.71784 | 0 |
| IRF1 | 22.62736 | 22.62736 | 0 |
| IRF2 | 8.269744 | 0 | 0 |
| IRF9 | 6.019136 | 0 | 0 |
| ISG15 | 67.27749 | 0 | 0 |
| MX1 | 58.9203 | 58.9203 | 0 |
| MX2 | 65.90186 | 65.90186 | 65.90186 |
| OAS1 | 311.1704 | 311.1704 | 311.1704 |
| OAS2 | 222.1048 | 222.1048 | 222.1048 |
| OAS3 | 5.651453 | 0 | 0 |
| OASL | 15.91084 | 15.91084 | 0 |
| SOCS1 | 16.0131 | 16.0131 | 0 |
| STAT2 | −1.11101 | 0 | 0 |

TABLE 5

ISG-DLDA Model Constants

|  | 22 ISGs | 12 ISGs | 6 ISGs |
| --- | --- | --- | --- |
| DLDA Model Constant | 670.61 | 503.76 | 384.89 |

The DLDA score for an individual future sample is obtained by the following algorithm:
1) obtain gene expression values for the 790 genes
2) add the value of 1.0 to each gene expression value
3) log 2 transform each value
4) calculate the within-sample mean and standard deviation based on the 790 log 2-transformed gene expression values from step 3
5) subtract the within-sample mean from each of the 790 values from step 3
6) divide each value from step 5 by the within sample standard deviation
7) select the values from step 6 associated with the ISG-signature genes
8) multiple each value from step 7 by the ISG coefficient from Table 4
9) total the values from step 8
10) if the ISG signature contains 22 ISGs, subtract 670.61 from the single value obtained from step 9; if the ISG signature contains 6 ISGs, subtract 384.89 from the single value obtained from step 9; and if the ISG signature contains 12 ISGs, subtract 503.76 from the single value obtained from step 9. This value is the DLDA score for this individual sample. The amounts subtracted are model constants (Table 5).

Example 4: Treating GBM

Cancer cells are obtained from a human identified as having GBM. The obtained GBM cancer cells are assessed for virotherapy responsiveness. In some cases, an ISG signature is obtained and used to determine a virotherapy permissive score (e.g., a DLDA score).

If a low or intermediate virotherapy permissive score is detected in the cancer cells, as compared to a control level, then the human is administered one or more oncolytic viruses (e.g., MV) to reduce the number of cancer cells present in the human. For example, when a DLDA score less than −250 is detected in the cancer cells, as compared to a control level, then the human is administered one or more oncolytic viruses (e.g., MV) to reduce the number of cancer cells present in the human. For example, when a DLDA score from about −250 to about 150 is detected in the cancer cells, as compared to a control level, then the human is administered one or more oncolytic viruses (e.g., MV) and one or more immunomodulatory agents (e.g., ruxolitinib) to reduce the number of cancer cells present in the human.

If a high virotherapy permissive score is detected in the cancer cells, as compared to a control level, then the human should be excluded from virotherapy treatments. For example, when a DLDA score greater than 150 is detected in the cancer cells, as compared to a control level, then the human should and administered one or more alternative cancer treatments (e.g., surgery, chemotherapy, and/or radiation) to reduce the number of cancer cells present in the human.

Example 5: Treating OvCa

Cancer cells are obtained from a human identified as having OvCa. The obtained cancer cells are assessed for virotherapy responsiveness. In some cases, an ISG signature is obtained and used to determine a virotherapy permissive score (e.g., a DLDA score).

If a low or intermediate virotherapy permissive score is detected in the cancer cells, as compared to a control level, then the human is administered one or more oncolytic viruses (e.g., MV) to reduce the number of cancer cells present in the human. For example, when a DLDA score less than −250 is detected in the cancer cells, as compared to a control level, then the human is administered one or more oncolytic viruses (e.g., MV) to reduce the number of cancer cells present in the human. For example, when a DLDA score from about −250 to about 150 is detected in the cancer cells, as compared to a control level, then the human is administered one or more oncolytic viruses (e.g., MV) and one or more immunomodulatory agents (e.g., ruxolitinib) to reduce the number of cancer cells present in the human.

If a high virotherapy permissive score is detected in the cancer cells, as compared to a control level, then the human should be excluded from virotherapy treatments. For example, when a DLDA score greater than 150 is detected in the cancer cells, as compared to a control level, then the human should and administered one or more alternative cancer treatments (e.g., surgery, chemotherapy, and/or radiation) to reduce the number of cancer cells present in the human.

Example 6: Converting Virotherapy Resistant Cancers into Virotherapy Responsive Cancers Upon viral infection, the host antiviral defense mechanism triggers IFN production and signaling through the JAK/STAT pathway to activate more than 300 ISGs (Silvennoinen et al., 1993 *Nature* 366:583-585). Therefore, the use of pharmacological agents to overcome resistance through chemical inhibition of the JAK/STAT pathway was explored. GBM39 cells were treated with 3 μM Jakafi for 48 hours prior to infection with MV-NIS (MOI 0.1). Virus production was significantly increased at 48 hours post-infection and nearly 1000-fold greater by 96 hours (FIG. 7a). The increased virus production and spread also led to increased cell killing in Jakafi pre-treated cells relative to control treated cells (FIG. 7b). A similar result was measured in 4 additional resistant and permissive lines (FIG. 8a,b).

Patient identified to have intermediate scores are treated with MV in combination with an immunomodulatory drug. An immunomodulatory drug that can a) inhibit the JAK/STAT pathway and thus suppress the expression of ISG and enhance replication, and/or b) enhance the immunostimulatory signal that viral replication creates. In some cases, an immunomodulatory drug that can suppress the expression of ISG and enhance replication for example can be Ruxolitinib. In some cases, an immunomodulatory drug that can enhance the immunostimulatory signal that viral replication creates can be pembrolizumab, nivolumab, atezolizumab, durvalumab, or ipilimumab.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating cancer in a mammal, wherein said method comprises:
   (a) identifying said mammal as having cancer cells that have a virotherapy permissive interferon (IFN)-stimulated gene (ISG) signature, wherein said virotherapy permissive ISG signature comprises a decreased level of expression of at least 6 ISGs selected from the group consisting of HLA-A, HLA-B, HLA-C, HLA-E, HLA-G, IFI27, IFI35, IFI6, IFIT1, IFIT3, IRF1, IRF2, IRF9, ISG15, MX1, MX2, OAS1, OAS2, OAS3, OASL, SOCS1, and STAT2, wherein said virotherapy permissive ISG signature indicates that said cancer cells are responsive to treatment with an oncolytic virus; and (b) administering said oncolytic virus to said mammal under conditions wherein the number of cancer cells within said mammal is reduced.

2. The method of claim 1, wherein said mammal is a human.

3. The method of claim 1, wherein said cancer is glioblastoma.

4. The method of claim 1, wherein said cancer is ovarian cancer.

5. The method of claim 1, wherein said oncolytic virus is a measles virus.

6. The method of claim 1, wherein said virotherapy permissive ISG signature comprises said decreased levels of expression as compared to control cells.

7. The method of claim 6, wherein said control cells comprise cancer cells resistant to oncolytic virus therapy.

8. The method of claim 1, wherein said ISG signature comprises OAS2, OAS1, IFI6, HLA-C, IFIT1, and MX2.

9. The method of claim 1, wherein said ISG signature comprises OAS2, OAS1, IFI6, HLA-C, IFIT1, MX2, HLA-A, IFIT3, OASL, HLA-G, MX1, and IRF1.

10. The method of claim 1, wherein said ISG signature comprises HLA-A, HLA-B, HLA-C, HLA-E, HLA-G, IFI27, IFI35, IFI6, IFIT1, IFIT3, IRF1, IRF2, IRF9, ISG15, MX1, MX2, OAS1, OAS2, OAS3, OASL, SOCS1, and STAT2.

* * * * *